US012617746B2

(12) United States Patent
Liang

(10) Patent No.: US 12,617,746 B2
(45) Date of Patent: May 5, 2026

(54) METHOD OF PREPARING TRITERPENOID COMPOUND

(71) Applicant: National Taiwan University, Taipei (TW)

(72) Inventor: Pi-Hui Liang, Taipei (TW)

(73) Assignee: National Taiwan University, Taipei (TW)

( * ) Notice: Subject to any disclaimer, the term of this patent is extended or adjusted under 35 U.S.C. 154(b) by 486 days.

(21) Appl. No.: 18/194,171

(22) Filed: Mar. 31, 2023

(65) Prior Publication Data

US 2023/0312447 A1 Oct. 5, 2023

Related U.S. Application Data

(60) Provisional application No. 63/325,792, filed on Mar. 31, 2022.

(51) Int. Cl.
*C07C 51/16* (2006.01)

(52) U.S. Cl.
CPC .......... *C07C 51/16* (2013.01); *C07C 2603/54* (2017.05)

(58) Field of Classification Search
CPC .................................................. C07C 2603/52
See application file for complete search history.

(56) References Cited

U.S. PATENT DOCUMENTS 9,828,326 B2 * 11/2017 Bishayee ............... A61K 31/19
2018/0346953 A1 12/2018 Liu et al.

FOREIGN PATENT DOCUMENTS

JP 6348530 B2 6/2018
WO 2020/263524 A1 12/2020

OTHER PUBLICATIONS

Fanping Cai et al., "*Medicago truncatula* Oleanolic-Derived Saponins Are Correlated with Caterpillar Deterrence," J. Chem. Ecol., 2017, vol. 43, pp. 712-724 (13 pages total).
Danylo Kaminskyy et al., "Synthesis of new potential anticancer agents based on 4-thiazolidinone and oleanane scaffolds," Med. Chem. Res. 2012, vol. 21, pp. 3568-3580 (13 pages total).
International Search Report issued Jul. 17, 2023 in Application No. PCT/US2023/017062.
Written Opinion issued Jul. 17, 2023 in Application No. PCT/US2023/017062.

* cited by examiner

*Primary Examiner* — Sikarl A Witherspoon
(74) *Attorney, Agent, or Firm* — Sughrue Mion, PLLC

(57) ABSTRACT

A method of preparing a triterpenoid compound of formula (I):

formula (I)

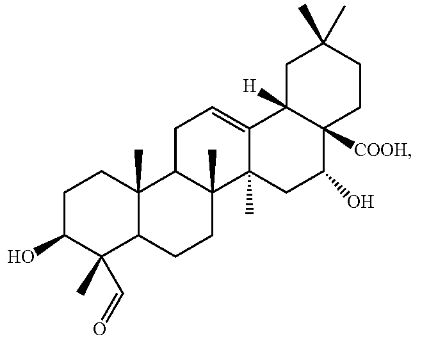

including a step of converting a compound of formula (II) into the compound of formula (I), formula (II)

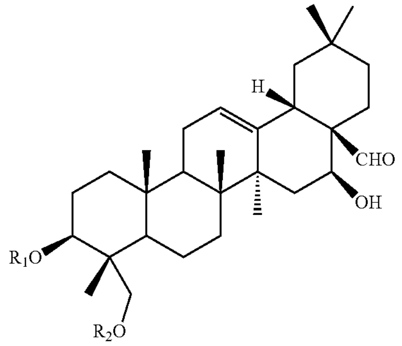

wherein $R_1$ and $R_2$ independently represent hydrogen or a protecting group selected from the group consisting of $C_1$-$C_8$ alkyl, allyl, $C_2$-$C_8$ alkenyl, C2-C8 alkynyl, ($C_6$-$C_{12}$)aryl($C_1$-$C_8$)alkyl, tri($C_1$-$C_8$)alkylsilyl, di($C_1$-$C_8$)alkyl($C_6$-$C_{12}$)arylsilyl, di($C_6$-$C_{12}$)aryl($C_1$-$C_8$)alkylsilyl ,tri($C_6$-$C_{12}$)arylsilyl, —C(O)$R_7$, and —C(O)O$R_8$, and each of which is substituted with from 0 to 4 substituents independently selected from the group consisting of hydroxy, cyano, halo, halo($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy, wherein $R_7$ and $R_8$ are independently $C_1$-$C_8$ alkyl or $C_6$-$C_{12}$ aryl.

12 Claims, 9 Drawing Sheets

Triterpenoid

Oleanolic

Ursane

Lupane

Dammarane

Steroid

Cholestane

Spirostane

Furostane

Cardenolide

Quillaic acid

Hederagenin

Oleanolic acid

6

7

8

9

10

Allyl Quillaic acid

Quillaic acid

Oleanolic acid (OA)

1

2

3

4

5

6

Hederagenin

12

14

11

13

15

METHOD OF PREPARING TRITERPENOID COMPOUND

CROSS-REFERENCE TO RELATED APPLICATIONS

This Application claims priority to U.S. Provisional Application No. 63/325,792, filed on Mar. 31, 2022. The entirety of the above-mentioned patent application is hereby incorporated by reference herein and made a part of this specification.

BACKGROUND

1. Technical Field

The present disclosure is related to a method of preparing of triterpenoid compound. More particularly, the present disclosure is related to a method of preparing of quillaic acid for triterpenoid saponin-based vaccine-adjuvant.

2. Description of Related Art

The name "saponin" is derived from the Latin word sapo, meaning soap-like foam generating ability, and the amphiphilic properties derived from the structure containing an isoprenoid-derived aglycone (a sapogenin), attached to one or more sugar chains by either an ether or ester linkage. Structural classification of saponins is primarily based on their sapogenin skeletons, which can be divided into two main groups, triterpenoid saponins and steroid saponins. Triterpenoid saponins are broadly distributed in dicotyledons, including four major skeletons, such as pentacyclic oleanane, ursane, lupane, and tetracyclic dammarane (FIG. 1*a*). Steroid saponins are mostly derived from monocotyledons, comprising of four major skeletons, such as tetracyclic cholestane, hexacyclic spirostane, pentacyclic furostane, and lactone-bearing cardenolide (FIG. 1*b*). Sugar-bearing sapogenins are categorized by numbers of sugar residue into monodesmosidic (one sugar residue), bidesmosidic (two sugar residues), and polydesmosidic saponins (three or more sugar residues).

In nature, saponins are found in plants and marine animals, where they are implicated in host defense against pathogens and herbivores. Since saponins are presented in many medicinal plants and Chinese herbal medicines, exhibiting a plethora of biological activities, including antifungal, antimicrobial, antiviral, anti-inflammatory, anticancer, antioxidant, and immunomodulatory effects, they can serve as a good starting point for the development of natural product-derived drugs. However, the mechanism and structure-activity-relationship (SAR) of saponins are poorly understood, and the isolation from plant to get appropriate amounts is sometimes troublesome and laborious due to microheterogeneity and scarcity of the molecules. As a result, applying organic synthesis method to generate artificial saponins is a promising way to efficiently expand the structure library and search for highly active compounds.

Oleanane type saponins are the most studied synthetic saponins, due to their promising pharmacological effects and high natural abundance. Referring to FIG. 2, common oleanane type skeletons modified with chemical approach are oleanolic acid, hederagenin, and quillaic acid. They have been isolated from enormous plant species as either a free triterpenoid or a saponin, and are particularly rich in Oleaceae family. Oleanane type saponins are reported to exhibit multiple biological activities, especially in antitumor, antiviral and immunomodulatory effect. However, toxicity triggered by hemolytic and membrane lysis effect is the major challenge in drug development, and the understanding of structure-toxicity-relationships is still in the early stage.

The saponins with immunomodulatory effects were categorized into upregulation and downregulation. Immune upregulation activities were majorly evaluated in quillaic-saponins, which were extensively studied for the enhancement of serum IgG production compared to GPI-0100 and QS-21 for the development of vaccine adjuvant and various derivatives based on quillaic acid have been developed.

QS-21 is an FDA-approved vaccine-adjuvant, which is widely used in treating infectious diseases and cancers. Contrary to versatile uses of QS-21, its natural source was limited. The traditional quillaic acid isolation methods need to extract from roots or barks. To preserve the natural source and make the application more sustainable, chemical synthesis of quillaic acid is necessary. However, chemical synthesis of quillaic acid started from protoescigenin was reported, it was 24-steps process to quillaic acid (Zeng et al., Chemical synthesis of quillaic acid, the aglycone of QS-21. *Org. Chem. Front.* 2021, 8, 748-753.). Besides chemical synthesis, biosynthesis has become a popular method in recent years. In 2021, Qian et al. identified the biosynthetic pathway of CYP716A262 and CYP72A567, which can provide alternative source of quillaic acid by starting the synthesis with the metabolite of β-amyrin. By transforming the *S. cerevisiae* strain BY-bAS with the CYP716A567 and CYP72A262 genes, it can produce 314.01 mg/L of quillaic acid. However, the method needed to clone the specific RNA sequences of CYP716A567 and CYP72A262 and could not be scaled up currently. The versatile C—H activation equips us with a new platform in pharmaceutical industry. Among terpenoid and steroid C—H functionalization, the methodology development and strategy design stand for the most important issue because low reactivity of aliphatic C—H bond and the abundant aliphatic C—H in the structures. To date, there are limited β-C($sp^3$)—H oxidation which have been reported to use in oleanane type terpenoids. The C-23 oxidation still exist some problem that makes it not practical to industrial use. For example, $[Ir(cod)(OMe)]_2$-catalyzed C-23 oxidation reported by Hartwig's group needs to be operated under glove box and sodium tetrachloropalladate (II) mediated C-23 oxidation reported by Baldwin's group needs to use stoichiometric palladium salt (FIG. 3A). For the reason mentioned above, the synthetic strategy design becomes a critical issue in terpenoids synthesis.

Directing group assisted C—H bond functionalization strategies have emerged during the past decades. Monodentate amides, pyridines or imines, as well as bidentate directing groups with Lewis basic properties that can control regioselectivity are utilized. Most of time, the directing groups are covalently bind to the substrate. However, removing of this kind of directing groups leads to redundant steps and low yield. Thus, native directing groups, traceless directing groups, transient directing groups and undirected C—H activation are developed to meet the need of economic efficiency.

Among the various directing group mentioned above, bidentate transient directing groups show its niche in C—H oxidation. The family of bidentate directing groups are categorized according to their coordination site, for instance, N,N-dentate (FIG. 4), N,O-dentate, and N,S-dentate auxiliaries. During the past decades, bidentate directing groups are widely used for transition-metal-catalyzed C—H bond functionalization reaction, since bidentate directing groups are easier for metal to coordinate over a monodentate and with tunable coordinating properties. In 2020, Yu et al. (Site-selective C—H hydroxylation of pentacyclic triterpenoids directed by transient chiral pyridine-imino groups. *Nat. Commun.* 2020, 11, 4371.) utilized chiral directing groups, (R/S)-(pyridine-2-yl)ethan-1-amine, successfully established a site-selective functionalization of triterpenoids (FIG. 3B). By forming a transient imine linkage, the bidentate directing groups form a complex with copper that directly hydroxylated C-22 and C-16 at triterpenoids D/E rings.

SUMMARY

The present disclosure utilizes a transient N,N-dentate directing strategy to access oleanane type terpenoids C—H bond hydroxylation. With the characteristics of easy removing and high selectivity, the synthetic steps can be reduced with this strategy. By combining two C—H activations, the present disclosure provides an environment-friendly and industry-practical quillaic acid synthetic method to replace the traditional extraction method to access quillaic acid.

The present disclosure provides a method of preparing a triterpenoid compound of formula (I):

formula (I)

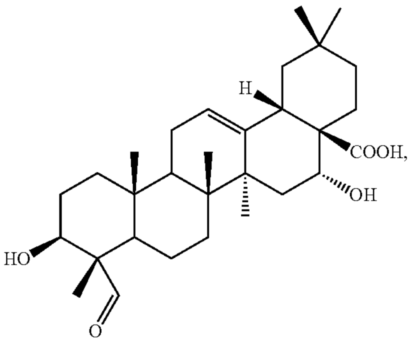

comprising a step of converting a compound of formula (II) into the compound of formula (I), formula (II)

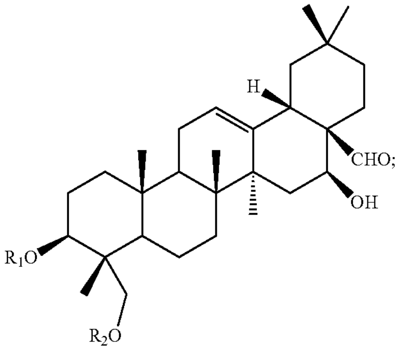

wherein $R_1$ and $R_2$ independently represent hydrogen or a protecting group selected from the group consisting of $C_1$-$C_8$ alkyl, allyl, $C_2$-$C_8$ alkenyl, $C_2$-$C_8$ alkynyl, ($C_6$-$C_{12}$)aryl($C_1$-$C_8$)alkyl, tri($C_1$-$C_8$)alkylsilyl, di($C_1$-$C_8$)alkyl($C_6$-$C_{12}$)arylsilyl, di($C_6$-$C_{12}$)aryl($C_1$-$C_8$)alkylsilyl ,tri($C_6$-$C_{12}$)arylsilyl, —C(O)$R_7$, and —C(O)O$R_8$, and each of which is substituted with from 0 to 4 substituents independently selected from the group consisting of hydroxy, cyano, halo, halo($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy, wherein $R_7$ and $R_8$ are independently $C_1$-$C_8$ alkyl or $C_6$-$C_{12}$ aryl.

In an exemplary embodiment of the present disclosure, the method further comprises a step of converting the compound of formula (II) into a compound of formula (III) through sequentially oxidizing the aldehyde group of formula (II) to a carboxyl group by oxidation, and forming an oxygen protecting group on one oxygen atom of the carboxyl group by attaching a protecting group, formula (II)

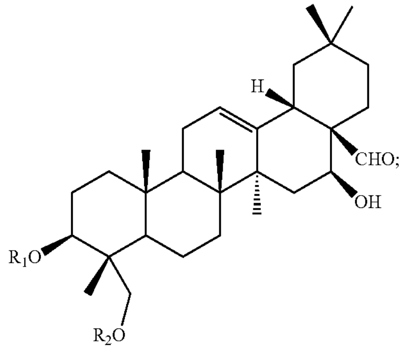

formula (III)

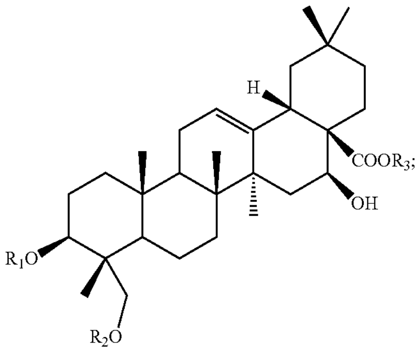

wherein $R_3$ is a protecting group selected from the group consisting of $C_1$-$C_8$ alkyl, allyl, $C_2$-$C_8$ alkenyl, $C_2$-$C_8$ alkynyl, ($C_6$-$C_{12}$)aryl($C_1$-$C_8$)alkyl, $C_6$-$C_{12}$ arylacyl, tri($C_1$-$C_8$)alkylsilyl, di($C_1$-$C_8$)alkyl($C_6$-$C_{12}$)arylsiyl, di($C_6$-$C_{12}$)aryl($C_1$-$C_8$)alkylsilyl and tri($C_6$-$C_{12}$)arylsilyl, and each of which is substituted with from 0 to 4 substituents independently selected from the group consisting of hydroxy, cyano, halo, halo($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy.

In an exemplary embodiment of the present disclosure, the method further comprises a step of converting the compound of formula (III) into a compound of formula (IV) through epimerization, deprotection and oxidation sequentially, formula (III)

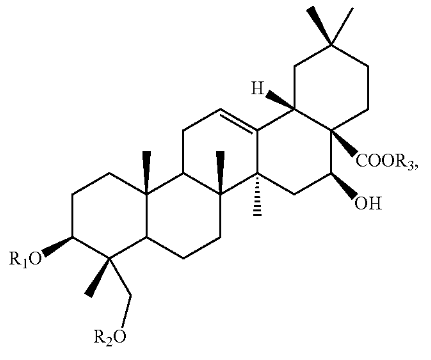

formula (IV)

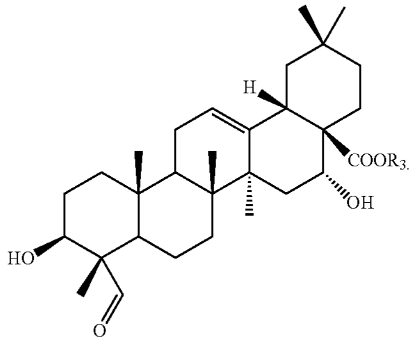

In an exemplary embodiment of the present disclosure, the method further comprises a step of subjecting the compound of formula (III) to epimerization at the carbon position where a hydroxyl group is attached to form a compound of formula (VI), and a step of converting the compound of formula (VI) to a compound of formula (IV) with deprotection and oxidation sequentially, formula (III)

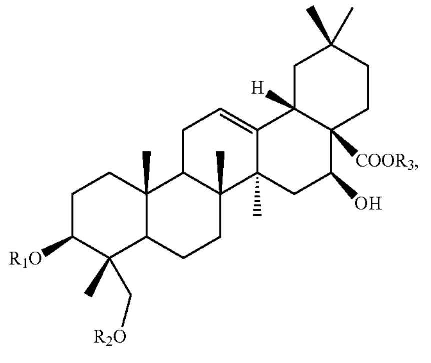

-continued formula (VI)

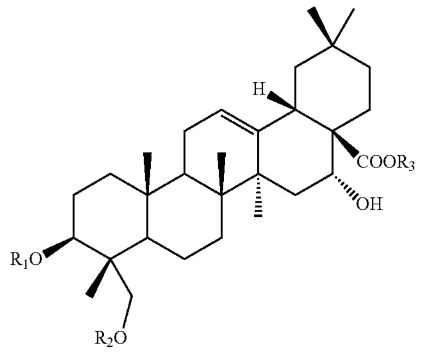

formula (IV)

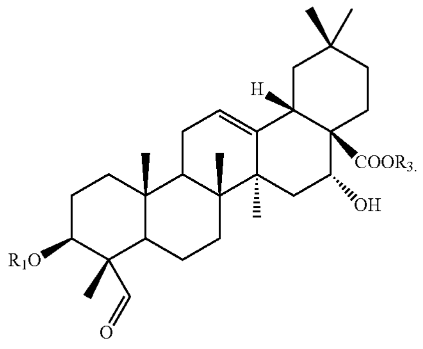

In the step of deprotection, $R_1$ and $R_2$ are removed from the compound of formula (VI).

In an exemplary embodiment of the present disclosure, the method further comprises a step of converting the compound of formula (IV) into the compound of formula (I) with deprotecting reaction, formula (IV)

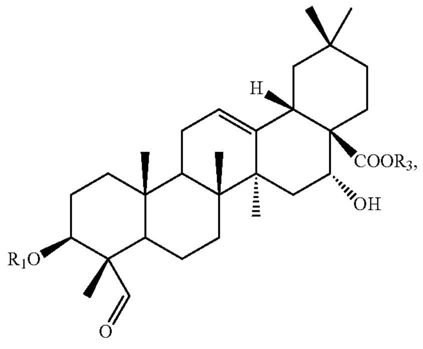

-continued formula (I)

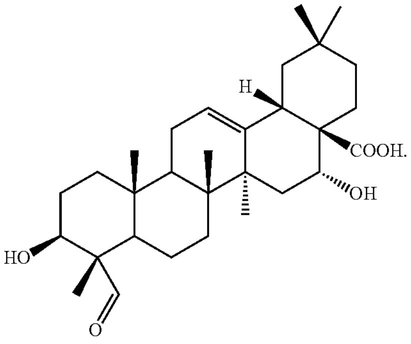

In the step of deprotection, $R_3$ is removed from the compound of formula (IV).

In an exemplary embodiment of the present disclosure, the method further comprises a step of converting a compound of formula (VII) into the compound of formula (II) through directing group introduction and C—H activation sequentially, formula (VII)

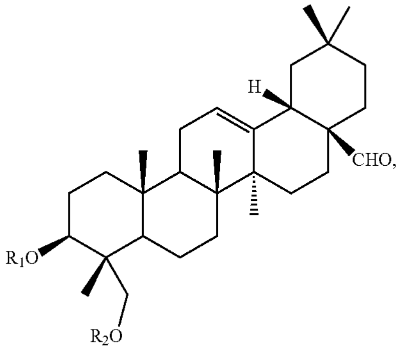

formula (II)

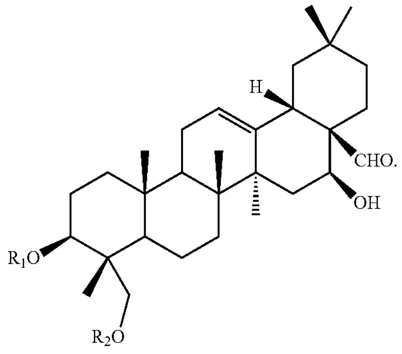

In another exemplary embodiment of the present disclosure, the method further comprises a step of converting the compound of formula (VII) into a compound of formula (VIII) by reacting the compound of formula (VII) with a compound of formula (a) through directing group introduction, and a step of converting the compound of formula (VIII) into the compound of formula (II) with C—H activation, formula (VII)

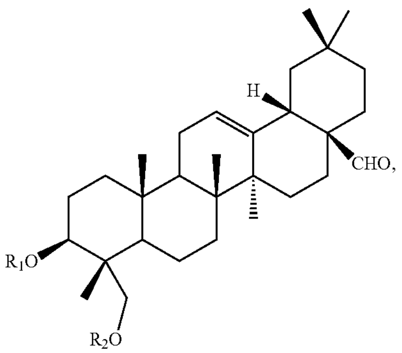

formula (VIII)

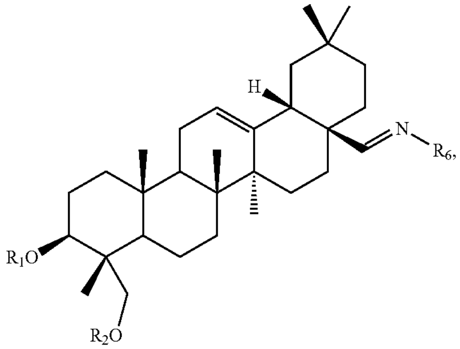

formula (II)

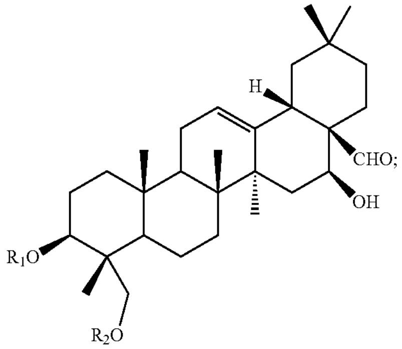

wherein $R_6$ represents

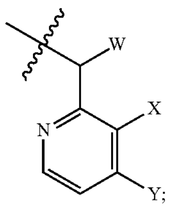

W is H or $C_1$-$C_8$ alkyl group and X and Y independently represent hydrogen, hydroxy, cyano, halo, $C_6$-$C_{12}$ aryl or $C_5$-$C_{12}$ heteroaryl, and wherein the compound of formula (a) represents

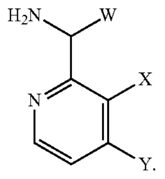

In another exemplary embodiment of the present disclosure, the method further comprises a step of converting oleanolic acid to the compound of formula (VII) through halolactone oxime formation, C—H activation, attaching protecting group and reduction sequentially, formula (VII)

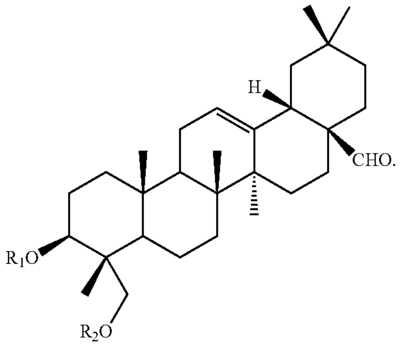

In another exemplary embodiment of the present disclosure, the compound of formula (VII) is obtained by converting a compound of formula (IX) into the compound of formula (VII) through reduction and optionally attaching protecting group sequentially, formula (IX)

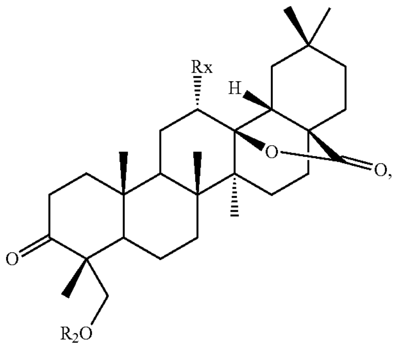

-continued formula (VII)

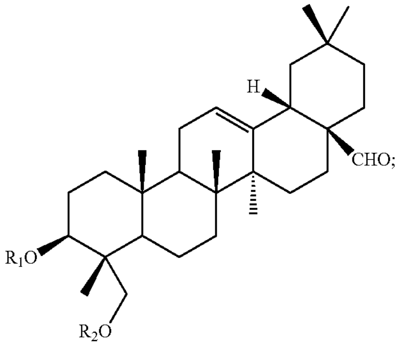

wherein Rx is F, Cl, Br or I.

In another exemplary embodiment of the present disclosure, the compound of formula (IX) is obtained by converting a compound of formula (X) into the compound of formula (IX) with C—H activation and attaching protecting group sequentially, formula (X)

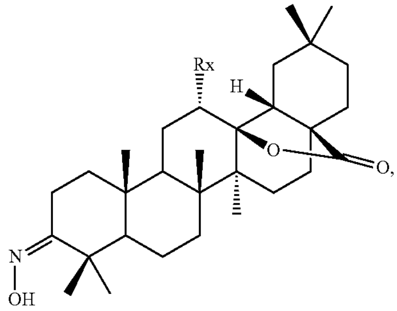

formula (IX)

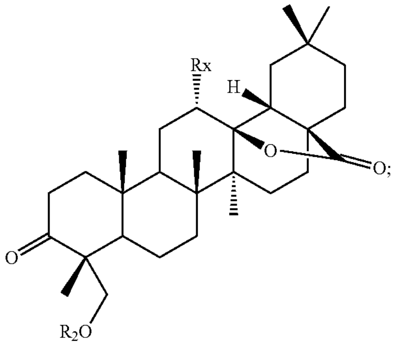

wherein Rx is F, Cl, Br or I.

In another exemplary embodiment of the present disclosure, the compound of formula (X) is obtained by converting Oleanolic acid into the compound of formula (X) with halolactone oxime formation, formula (X)

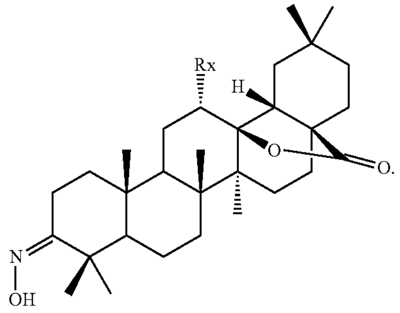

In another exemplary embodiment of the present disclosure, the method further comprises a step of converting Hederagenin into the compound of formula (VII) through attaching a protecting group, reduction and oxidation sequentially, formula (VII)

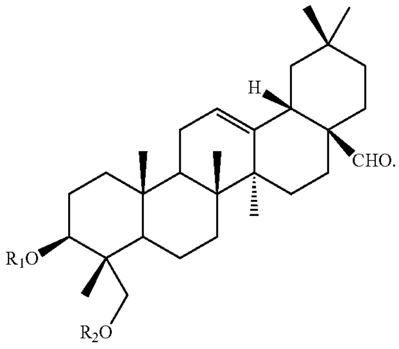

In another exemplary embodiment of the present disclosure, the method further comprises a step of oxdizing a compound of formula (XI) into the compound of formula (VII), formula (XI)

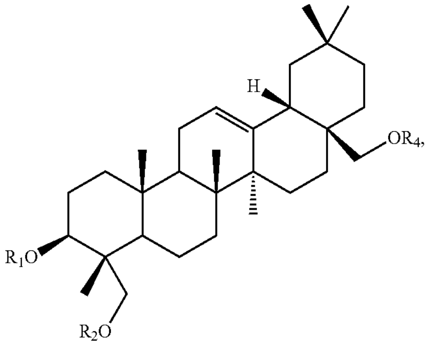

-continued formula (VII)

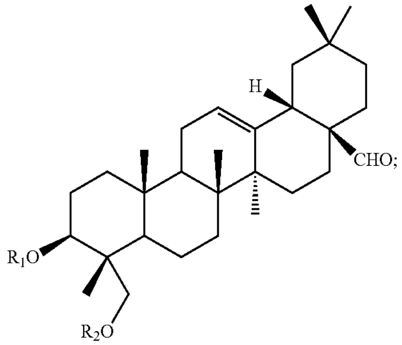

wherein $R_4$ is hydrogen or a protecting group selected from the group consisting of $C_1$-$C_8$ alkyl, allyl, $C_2$-$C_8$ alkenyl, $C_2$-$C_8$ alkynyl, $(C_6$-$C_{12})$aryl $(C_1$-$C_8)$alkyl, $C_6$-$C_{12}$ arylacyl, tri$(C_1$-$C_8)$alkylsilyl, di$(C_1$-$C_8)$alkyl$(C_6$-$C_{12})$arylsilyl, di$(C_6$-$C_{12})$aryl$(C_1$-$C_8)$alkylsilyl and tri$(C_6$-$C_{12})$arylsilyl, each of which is substituted with from 0 to 4 substituents independently selected from the group consisting of hydroxy, cyano, halo, halo$(C_1$-$C_6)$alkyl, halo$(C_1$-$C_6)$alkyloxy, $(C_1$-$C_6)$alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy.

In another exemplary embodiment of the present disclosure, the method further comprises a step of reducing a compound of formula (XII) to the compound of formula (XI), formula (XII)

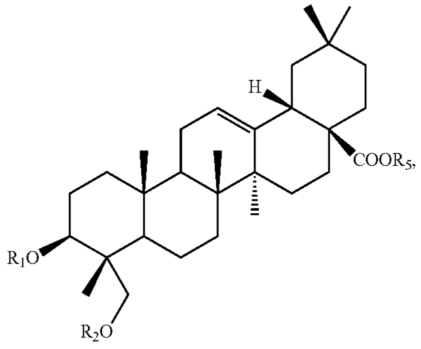

formula (XI)

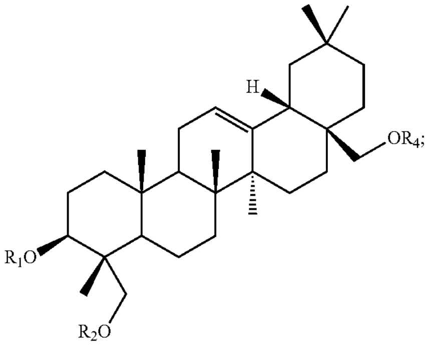

wherein $R_5$ is hydrogen or a group selected from the group consisting of $C_1$-$C_8$ alkyl, allyl, $C_2$-$C_8$ alkenyl, $C_2$-$C_8$ alkynyl, $(C_6$-$C_{12})$aryl $(C_1$-$C_8)$alkyl, $C_6$-$C_{12}$ arylacyl, tri$(C_1$-$C_8)$alkylsilyl, di$(C_1$-$C_8)$alkyl$(C_6$-$C_{12})$arylsilyl, di$(C_6$-$C_{12})$aryl$(C_1$-$C_8)$alkylsilyl and tri$(C_6$-$C_{12})$arylsilyl, each of which is substituted with from 0 to 4 substituents independently selected from the group consisting of hydroxy, cyano, halo, halo($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy.

In another exemplary embodiment of the present disclosure, the method comprises a step of converting Hederagenin into the compound of formula (XII) through attaching protecting groups on the hydroxyl groups of Hederagenin, formula (XII)

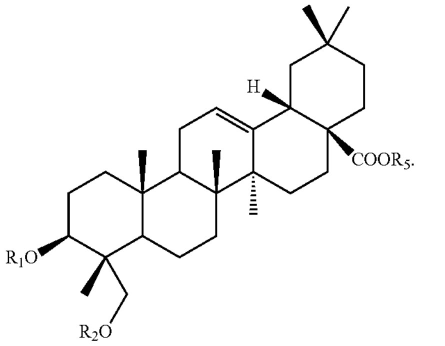

DETAILED DESCRIPTION

Figure 1A:
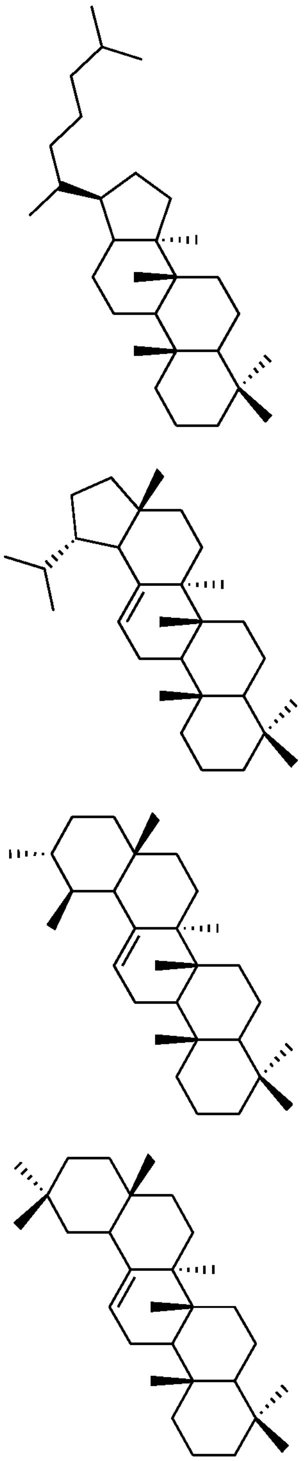
FIG. 1*a* shows major representative structures of triterpenoid saponins.
Figure 1B:
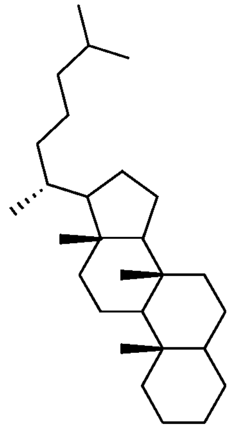
FIG. 1*b* shows major representative structures of steroid saponins.
Figure 1B:
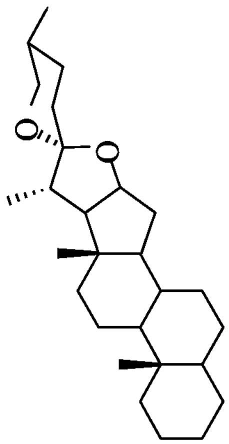
Figure 1B:
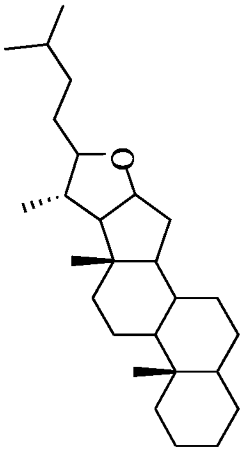
Figure 1B:
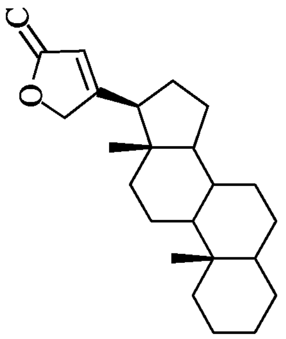
Figure 2:
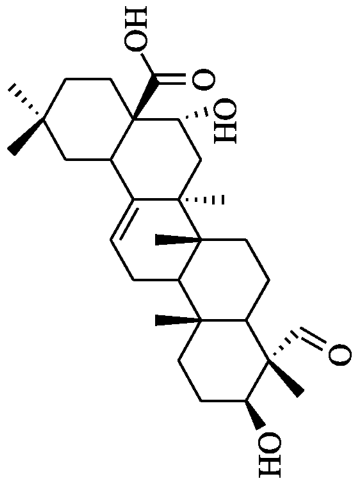
FIG. 2 shows representative structures of oleanane type saponins.
Figure 2:
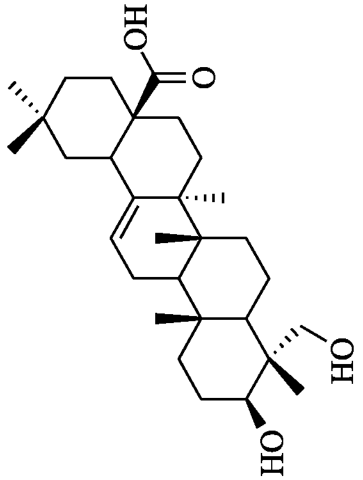
Figure 2:
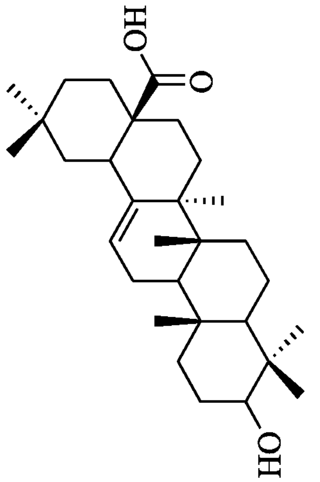
Figure 3A:
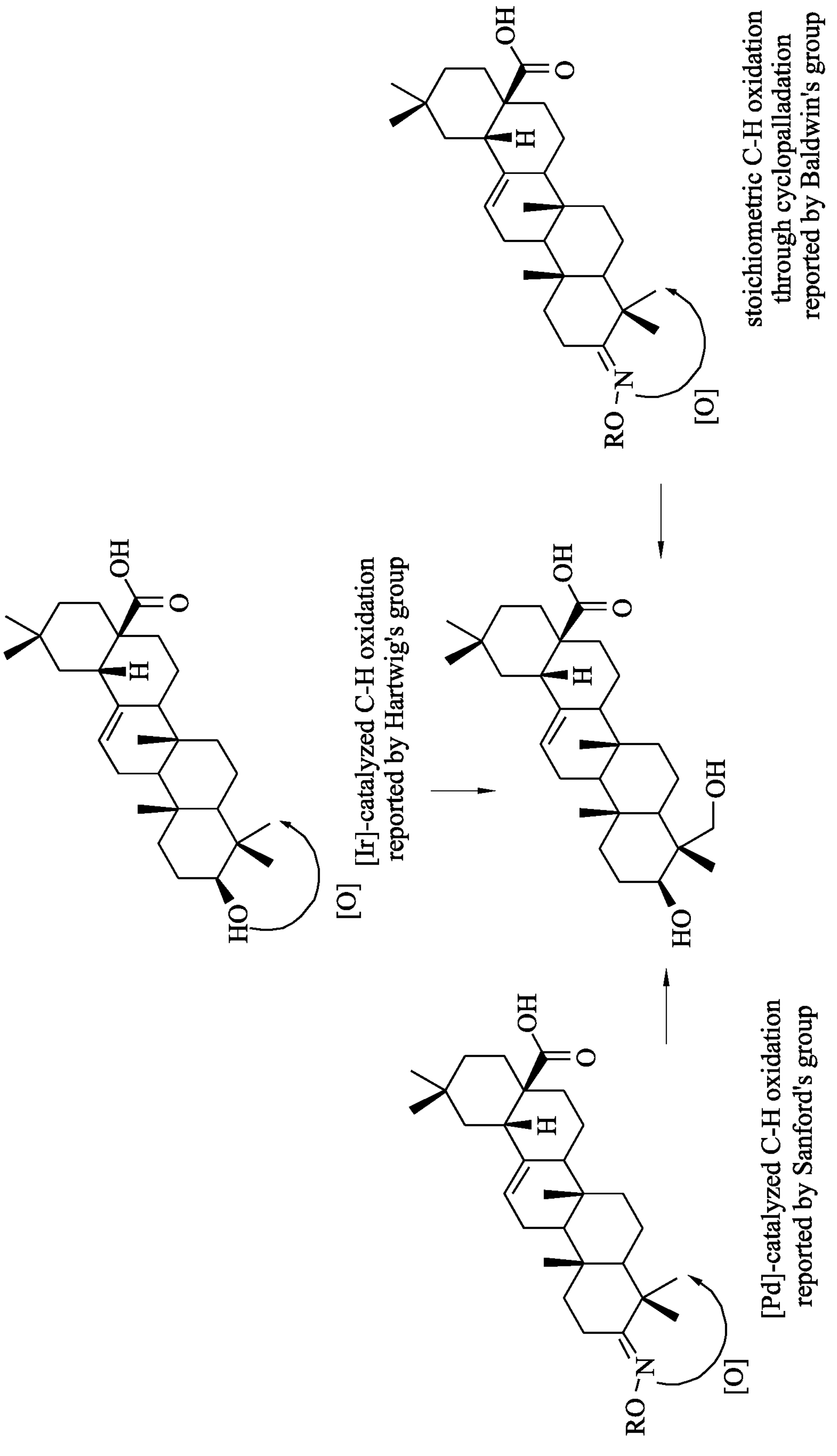
FIG. 3A shows strategies toward triterpenoid C-23 oxidation.
Figure 3B:
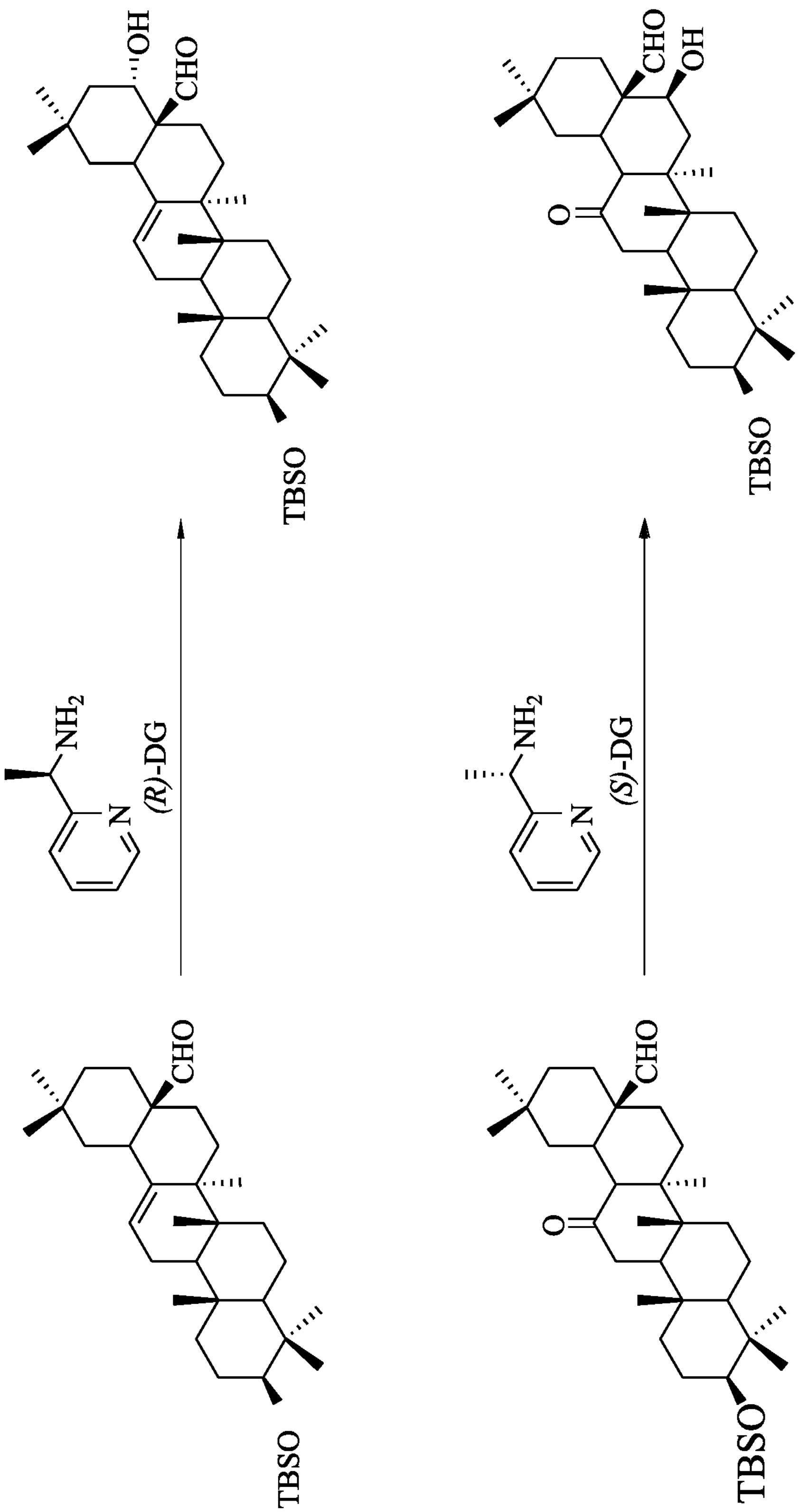
FIG. 3B shows schemes that C-22 and C-16 at triterpenoids D/E rings are directly hydroxylated by using bidentate directing groups.
Figure 4:
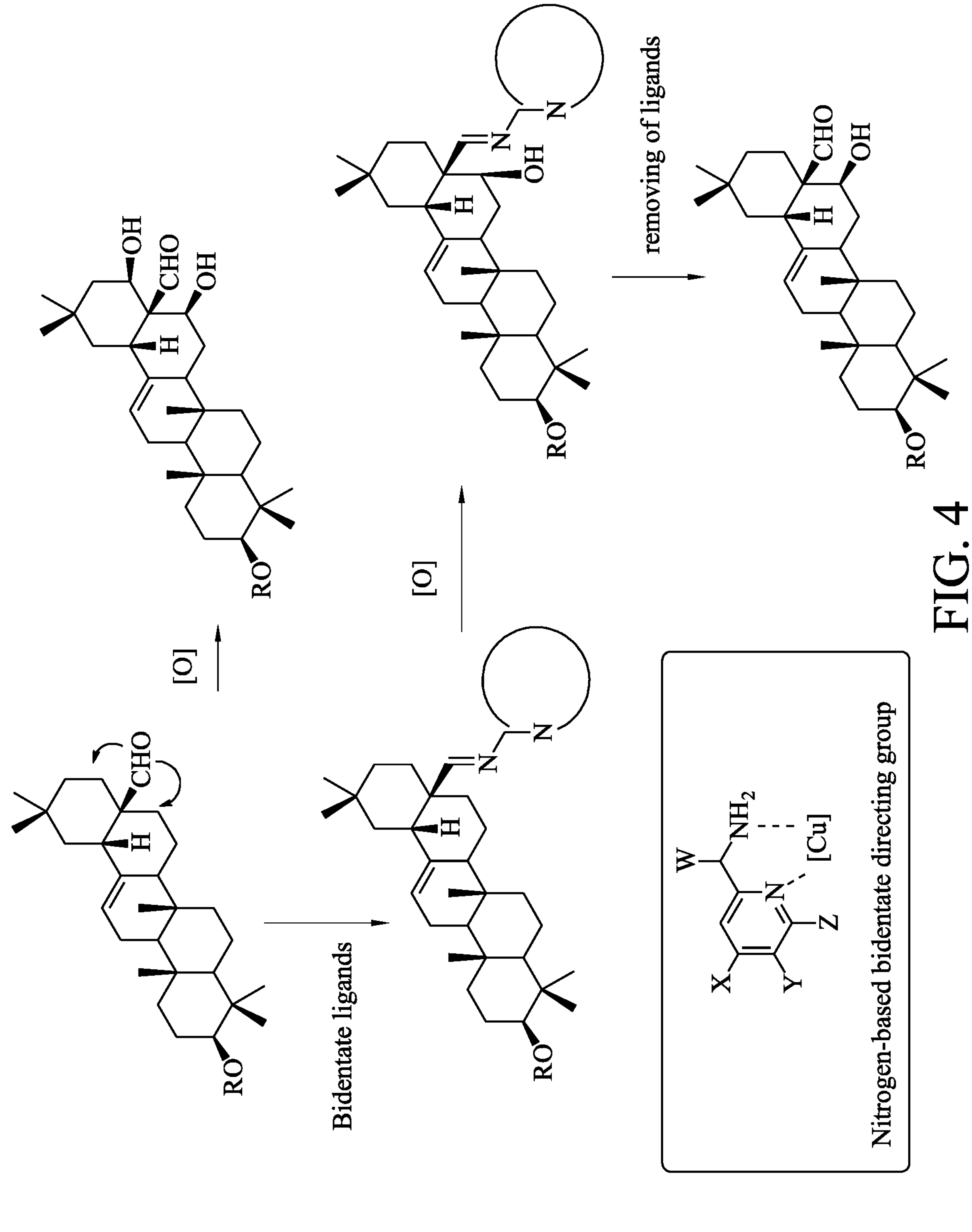
FIG. 4 shows a scheme for using bidentate directing group to improve C-16 oxidation.

The following disclosure provides many different embodiments, or examples, for implementing different features of the present disclosure. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. Unless stated otherwise specifically in the specification, an alkyl group may be optionally substituted.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms. The double bond of an alkenyl group can be unconjugated or conjugated with another unsaturated group. Non-limiting examples of alkenyl groups include vinyl, allyl, butenyl, pentenyl, hexenyl, butadienyl, pentadienyl, hexadienyl, 2-ethylhexenyl, and cyclopent-1-en-1-yl. Unless stated otherwise specifically in the specification, an alkenyl group may be optionally substituted.

The term "alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively. The triple bond of an alkynyl group can be unconjugated or conjugated with another unsaturated group. Non-limiting examples of alkynyl groups include ethynyl, propynyl, butynyl, pentynyl, and hexynyl. Unless stated otherwise specifically in the specification, an alkynyl group may be optionally substituted.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl.

By "alkoxy" as used herein, is meant an alkyl group attached via an oxygen bridge. Alkoxy groups include Ci-Csalkoxy and $C_1$-$C_4$alkoxy groups, which have from 1 to 8 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups.

The term "aryl" refers hydrocarbon ring system groups comprising at least 6 carbon atoms or 6 to 12 carbon atoms and at least one aromatic ring. The aryl group may be a monocyclic, bicyclic, tricyclic or tetracyclic ring system, which may include fused or bridged ring systems. Non-limiting examples of aryl groups include aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted.

The term "heteroaryl" or "heteroaromatic" means an aromatic mono-, bi-, or polycyclic ring incorporating one or more (for example 1 to 4, particularly 1, 2 or 3) heteroatoms selected from nitrogen, oxygen or sulfur. The term "heteroaryl" includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-C12-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—-$C_2$-$C_8$-alkynyl, —O—-$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$CO_2$—$C_3$-$C_{12}$-cycloalkyl, —$OCO_2$-aryl, —$OCO_2$-heteroaryl, —$OCO_2$-heterocycloalkyl, —$OCO_2$—$C_1$-$C_{12}$ alkyl, —$OCO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$-$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, 13 $NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC (NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C (NH)NH-heteroaryl, —C (NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S (O)-heteroaryl, —S (O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted. In one embodiment of the present disclosure, the substituents may be selected from the group consisting of hydroxy, cyano, halo, halo($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_3$-$C_7$ cycloalkyl and $C_1$-$C_6$ alkoxy.

The phrase "substituted with from 0 to X substituents" also indicated by "optionally substituted" refers to groups that are unsubstituted or substituted by other than hydrogen at one or more available positions, typically 1, 2, 3, 4, 5 or 6 positions, by one or more suitable groups (which may be the same or different), where X is the maximum number of permissible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents).

The term "halo" or "halogen" refers to fluoro, chloro, bromo and iodo.

The term "protecting group" intends any protecting group for an alcohol(s) well known in the art. Non-limiting examples include 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TB DPS).

The term "deprotection", "deprotecting" or the like intends removal of the protecting group by any conventional means known to the skilled artisan. It will be readily apparent that the conditions for deprotecting depend upon which protecting group is used.

The term "C—H activation" (known as C—H bond activation and sometimes used interchangeably with C—H functionalization) is a series of mechanistic processes by which stable carbon-hydrogen bonds in organic compounds are cleaved. The purpose is to enable functionalization of these molecules, leading to the synthesis of more complex intermediate or product compounds often containing C—O, C—C and C—N bonds. The ability to cleave the C—H bond enables inexpensive feedstock molecules to be transformed into commercially valuable molecules. Directed C—H activation enables selectivity and specificity in the synthesis of more complex molecules of importance in pharmaceutical and fine chemical applications.

The term "directing group" (DG) is a sub stituent on a molecule or ion that facilitates reactions by interacting with a reagent. The term is usually applied to C—H activation of hydrocarbons, where it is defined as a "coordinating moiety (an "internal ligand"), which directs a metal catalyst into the proximity of a certain C—H bond".

The term "halolactone" refers to form a lactone with added halogen by halolactonization. Halolactonization is an intramolecular variant of the halohydrin synthesis reaction. The reaction was first reported by M. J. Bougalt in 1904 and has since become one of the most effective ways to synthesize lactones.

The term "oxime" refers to a compounds of structure $R_2C{=}NOH$ derived from condensation of aldehydes or ketones with hydroxylamine. Oximes from aldehydes may be called aldoximes; those from ketones may be called ketoximes.

Preparation of Triterpenoid Compound

In one embodiment of the present disclosure, compounds of formula (X) may be prepared with halolactone oxime formation in accordance with Scheme 1. Oleanolic acid (OA) is added to solvents such as dichloromethane (DCM) and pyridine. Then halogenating agent (such as N-bromosuccinimide (NBS)) used for halolactonization, oxidizing agent (such as trichloroisocyanuric acid (TCCA)) used for oxidation of C-3-OH and oximating agent (such as hydroxylamine hydrochloride ($HONH_2{\cdot}HCl$)) used for oxime formation in halolactone oxime formation are added sequentially at 15+30° C., such as 15, 16, 17, 18, 19, 20, 21, 22, 23, 24, 25, 26, 27, 28, 29 and 30° C., to obtain compounds of formula (X). In one embodiment of the present disclosure, the halogenating agent is added and kept stirring for 1~hours, such as 1, 1.5 and 2 hours; the oxidizing agent is added and kept stirring for 1.5~2.5 hours, such as 1.5, 2 and 2.5 hours; and the oximating agent is added and kept stirring for 0.5~1.5 hours, such as 0.5, 1 and 1.5 hours.

-continued

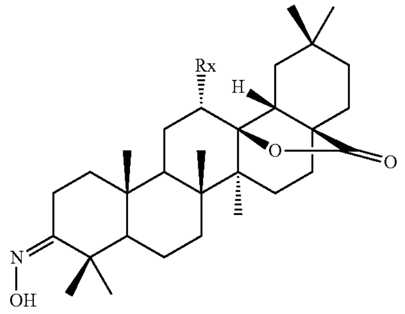

(X)

In one embodiment of the present disclosure, compounds of formula (IX) may be prepared with C—H activation and attaching protecting group sequentially in accordance with Scheme 2. The compounds of formula (X) is dissolved in co-solvent such as acetic anhydride ($Ac_2O$)/ Acetic acid (AcOH), and then palladium metal catalyst (such as, but not limited to, $PdCl_2$, $Pd(allyl)Cl_2$ and $Pd(OAc)_2$) and oxidizing agent (such as phenyliodine(III) diacetate(PIDA)) are added sequentially at 40~50° C., such as 40, 41, 42, 43, 44, 45, 46, 47, 48, 49 and 50° C. Then, the mixture is added co-solvent such as tetrahydrofuran (THF)/acetone in the presence of acid such as HCl at 50~60° C., such as 50, 51, 52, 53, 54, 55, 56, 57, 58, 59 and 60° C., to obtain compounds of formula (IXa). The compounds of formula (IXa) are dissolved in solvent such as dimethylformamide (DMF), dichloromethane (DCM) or dimethyl sulfoxide (DMSO) under $N_2$ atmosphere. Imidazole and protecting group compound such as tert-butyldimethylsilyl chloride (TBSCl) are added sequentially between −4~4° C., such as -4, -3, -2, -1, 0, 1, 2, 3 or 4° C., then stirred at 15~30° C., such as 15, 16, 17, 18, 19, 20, 21, 22, 23, 24, 25, 26, 27, 28, 29 and 30° C., to obtain compounds of formula (IX). In one embodiment of the present disclosure, the palladium metal catalyst is added and kept stirring for 1~2 minutes, such as 1, 1.5 and 2 minutes; the oxidizing agent is added and kept stirring for 7.5~8.5 hours, such as 7.5, 8 and 8.5 hours; and the acid is added and kept stirring for 7.5~8.5 hours, such as 7.5, 8 and 8.5 hours. In one embodiment of the present disclosure, the imidazole and protecting group compound are added and kept stirring for 3.5~4.5 hours, such as 3.5, 4 and 4.5 hours.

Scheme 1

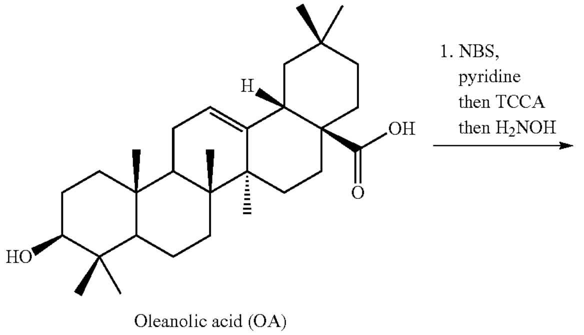

Oleanolic acid (OA)

Scheme 2

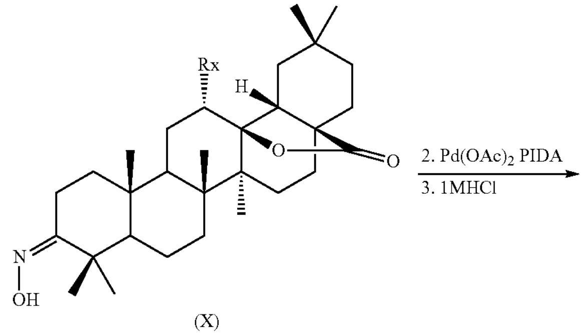

(X)

-continued

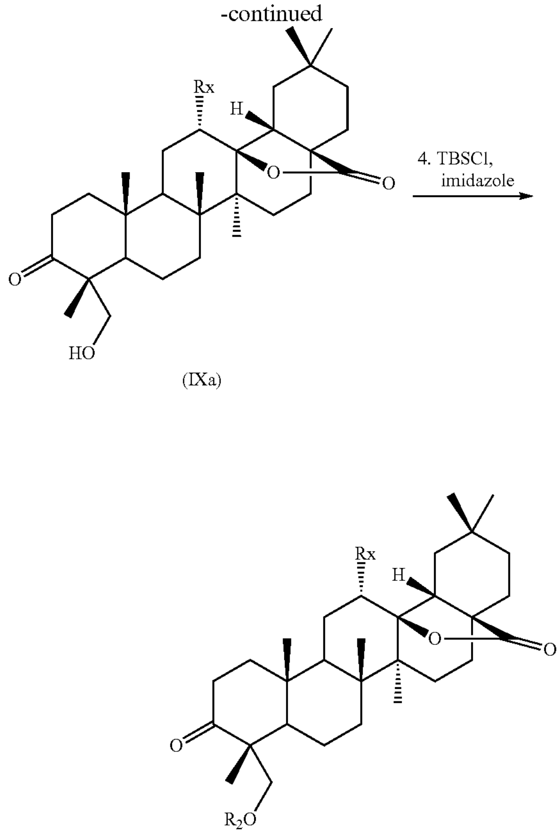

(IXa)

(IX)

In one embodiment of the present disclosure, compounds of formula (VII) may be prepared through reduction and optionally attaching protecting group sequentially in accordance with Scheme 3. The reducing agent such as lithium tri-tert-butoxyaluminum hydride (LTBA) dissolved in a solvent such as tetrahydrofuran (THF) is added to compounds of formula (IX) at 15~30° C., such as 15, 16, 17, 18, 19, 20, 21, 22, 23, 24, 25, 26, 27, 28, 29 and 30° C., and then the mixture is cooled to about −82° C.~−75° C., such as −82, −81, −80, −79, −78, −76 or −75° C., and added reducing agent such as diisobutylaluminum hydride (DIBAL-H). Catalyst AcOH/Zn is added at 45~55° C., such as 45, 46, 47, 48, 49, 50, 51, 52, 53, 54 or 55° C., and cooled to 15~30° C., such as 15, 16, 17, 18, 19, 20, 21, 22, 23, 24, 25, 26, 27, 28, 29 and 30° C., to obtain compounds of formula (VIIa). Compounds of formula (VIIa) are dissolved in a solvent such as dimethylformamide (DMF), dichloromethane (DCM) or dimethyl sulfoxide (DMSO) under $N_2$ atmosphere. Imidazole and protecting group compound such as tert-butyldimethylsilyl chloride (TBSCl) are added sequentially between −4~4° C., such as −4, −3, −2, −1, 0, 1, 2, 3 or 4° C., then stirred at 15~30° C., such as 15, 16, 17, 18, 19, 20, 21, 22, 23, 24, 25, 26, 27, 28, 29 and 30° C., to obtain compounds of formula (VII). In one embodiment of the present disclosure, the reducing agent is added and kept stirring for 0.5~2 hours, such as 0.5, 1, 1.5 and 2 hours; and the catalyst is added and kept stirring for 0.5~1.5 hours, such as 0.5, 1 and 1.5 hours. In one embodiment of the present disclosure, the imidazole and protecting group compound are added and kept stirring for 3.5~4.5 hours, such as 3.5, 4 and 4.5 hours.

Scheme 3

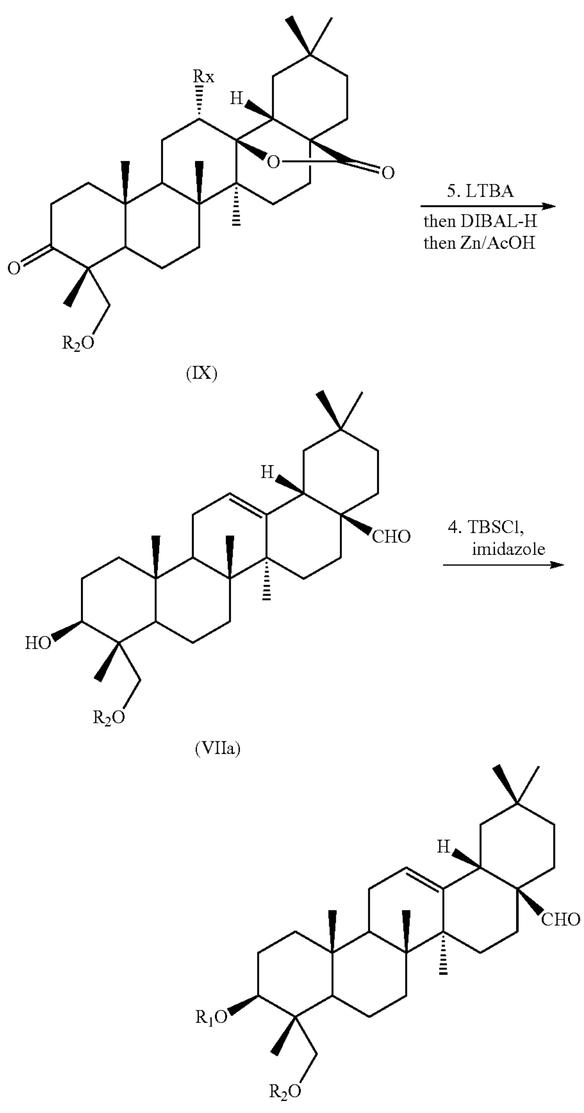

(IX)

(VIIa)

(VII)

In one embodiment of the present disclosure, further comprises a step of converting the compound of formula (VII) into a compound of formula (VIII) by reacting the compound of formula (VII) with a compound of formula (a) through directing group introduction, and a step of converting the compound of formula (VIII) into the compound of formula (II) with C—H activation in accordance with Scheme 4. Compounds of formula (VII) is reacted with compound of formula (a) in the presence of a solvent such as toluene and warmed to 75~85° C., such as 75, 76, 77, 78, 79, 80, 81, 82, 83, 84 and 85° C., to afford compounds of formula (VIII). The cupric salt such as $Cu(OTf)_2$ or $(CuOTf)_2{\cdot}C_6H_6$ and Na ascorbate are added to the mixture of compounds of formula (VIII), and then a solvent such as methanol/acetone is added to the mixture and stirred at 15~30° C., such as 15, 16, 17, 18, 19, 20, 21, 22, 23, 24, 25, 26, 27, 28, 29 and 30° C. Then the 02 balloon is made to bubble through the mixture, and warmed to 45~55° C., such as 45, 46, 47, 48, 49, 50, 51, 52, 53, 54 or 55° C., to obtain compound of formula (II). The compounds of formula (a)

are available from commercial sources or may be synthesized from commercially available precursors using established protocols known in the art of synthetic organic chemistry, or variations thereon as appreciated by those skilled in the art. In one embodiment of the present disclosure, the compound of formula (a) is added and kept stirring for 1.5~2.5 hours, such as 1.5, 2 and 2.5 hours. In one embodiment of the present disclosure, the cupric salt and Na ascorbate are added and kept stirring for 1.5~2.5 hours, such as 1.5, 2, and 2.5 hours.

Scheme 4

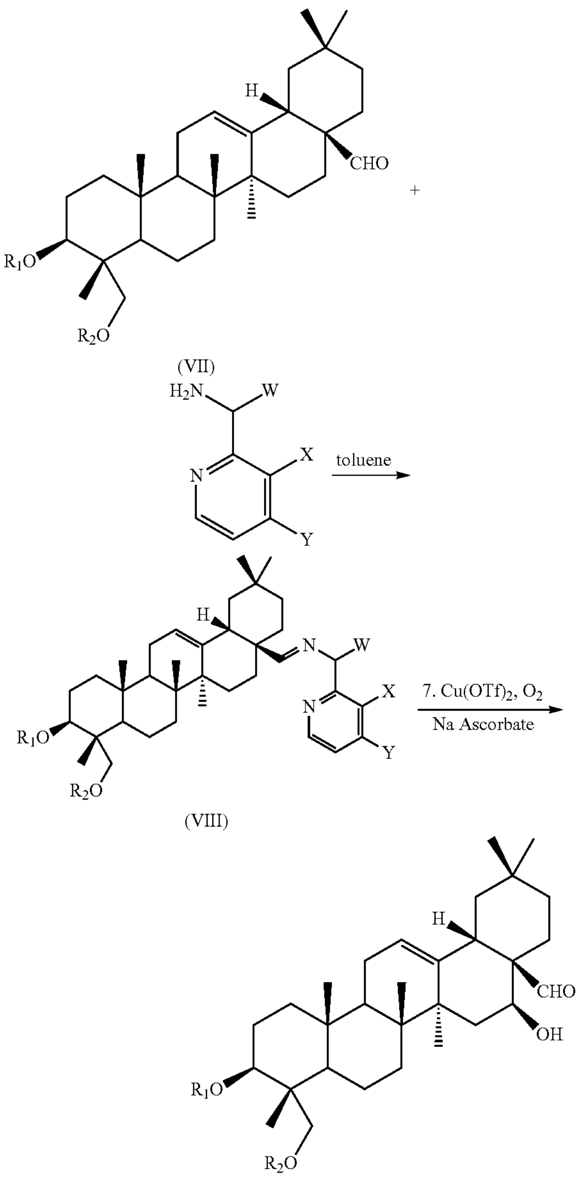

(VII)

(VIII)

(II)

In another embodiment of the present disclosure, further comprises a step of converting the compound of formula (VII) into a compound of formula (VIII) by reacting the compound of formula (VII) with a compound of formula (a) through directing group introduction, and a step of converting the compound of formula (VIII) into the compound of formula (II) with C—H activation in accordance with Scheme 4-1. A mixture containing compounds of formula (VII) and an organic-soluble acid catalyst, such as p-toluenesulfonic acid monohydrate (TsOH), is reacted with compound of formula (a) in the presence of a solvent such as toluene and warmed to 75~85° C., such as 75, 76, 77, 78, 79, 80, 81, 82, 83, 84 and 85° C., to afford compounds of formula (VIII). The mixture of cupric salt such as Copper(II) nitrate trihydrate ($Cu(NO_3)_2 \cdot 3H_2O$) and compounds of formula (VIII) is added to a solvent such as THF/methanol/acetone and stirred at 15~30° C., such as 15, 16, 17, 18, 19, 20, 21, 22, 23, 24, 25, 26, 27, 28, 29 and 30° C. Then, an oxidizing agent such as hydrogen peroxide ($H_2O_2$) is added to the reaction mixture to obtain compound of formula (II). In one embodiment of the present disclosure, the cupric salt and compounds of formula (VIII) are added and kept stirring for 0.5~1.5 hours, such as 0.5, 1, and 1.5 hours; and the oxidizing agent is added and kept stirring for 23~25 hours, such as 23, 24, and 25 hours.

Scheme 4-1

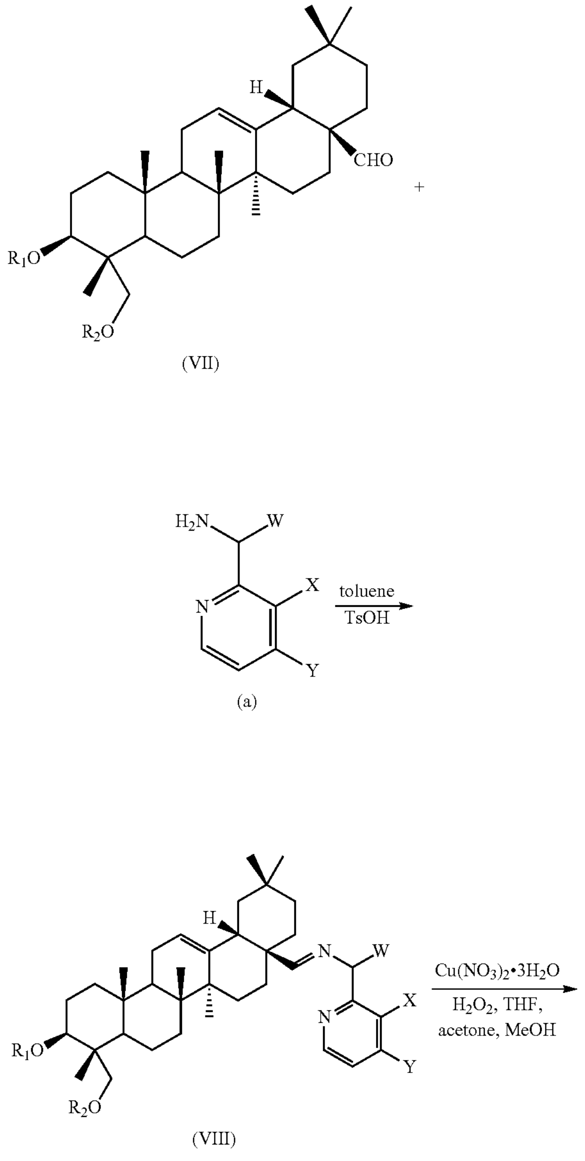

(VII)

(a)

(VIII)

-continued

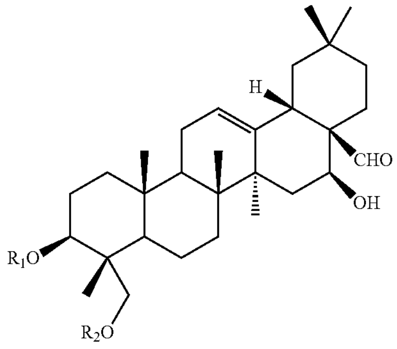

(II)

-continued

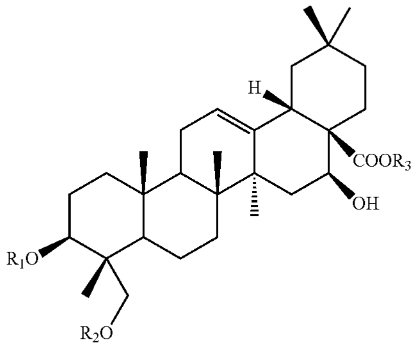

(III)

In one embodiment of the present disclosure, compounds of formula (III) may be prepared through sequentially oxidizing the aldehyde group of formula (II) to a carboxyl group by oxidation, and forming an oxygen protecting group on one oxygen atom of the carboxyl group by attaching an oxygen protecting group in accordance with Scheme 5. Compounds of formula (II) dissolved in a solvent such as DMSO/tert-Butanol are added a solution containing an oxidizing agent such as $NaClO_2$ and a buffer such as $NaH_2PO_4 \cdot H_2O$ at 15~30° C., such as 15, 16, 17, 18, 19, 20, 21, 22, 23, 24, 25, 26, 27, 28, 29 and 30° C. The mixture is then acidified with solution such as aqueous HCl to obtain a crude mixture. The crude mixture is dissolved in a solvent such as $THF/H_2O$, and then a protecting group reagent such as allyl bromide, a catalyst such as tetra-n-butylammonium iodide and a reaction reagent such as $K_2CO_3$ are added subsequently between 60~70° C., such as 60, 61, 62, 63, 64, 65, 66, 67, 68, 69 and 70° C., to obtain compounds of formula (III). In one embodiment of the present disclosure, the oxidizing agent is added and kept stirring for 3.5~4.5 hours, such as 3.5, 4, and 4.5 hours; and the protecting group reagent is added and kept stirring for 3.5~4.5 hours, such as 3.5, 4, and 4.5 hours.

Scheme 5

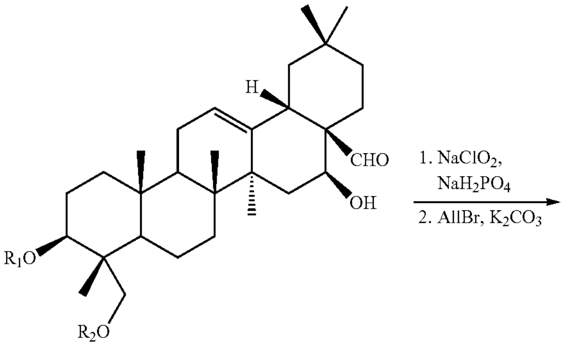

(II)

In one embodiment of the present disclosure, further comprises a step of subjecting the compound of formula (III) to epimerization at the carbon position where a hydroxyl group is attached to form a compound of formula (VI), and a step of converting the compound of formula (VI) to a compound of formula (IV) with deprotection and oxidation sequentially in accordance with Scheme 6. Compounds of formula (III) are dissolved in solvent such as dimethylformamide (DMF), dichloromethane (DCM) or dimethyl sulfoxide (DMSO), and then an oxidizing agent such as Dess Martin periodinane (DMP) is added at 15~30° C., such as 15, 16, 17, 18, 19, 20, 21, 22, 23, 24, 25, 26, 27, 28, 29 and 30° C., to obtain a compound. The compound from the previous step is dissolved in a solvent such as ethanol or isopropanol, and then a reducing agent such as sodium borohydride ($NaBH_4$) is added at 15~30° C., such as 15, 16, 17, 18, 19, 20, 21, 22, 23, 24, 25, 26, 27, 28, 29 and 30° C., to obtain compounds of formula (VI). Compounds of formula (VI) are dissolved in a solvent, such as THF, containing deprotecting reagent such as tetra-n-butylammonium fluoride (TBAF) at 45~55° C., such as 45, 46, 47, 48, 49, 50, 51, 52, 53, 54 or 55° C., to obtain compounds of formula (VIa). Compounds of formula (VIa) are dissolved in a solvent such as dimethylformamide (DMF), dichloromethane (DCM) or dimethyl sulfoxide (DMSO), and catalyst such as 2,2,6,6-Tetramethylpiperidine-1-oxyl (TEMPO) and potassium bromide (KBr) are added. Then a solution containing an oxidizing agent such as sodium hypochlorite (NaOCl) is added at 15~30° C., such as 15, 16, 17, 18, 19, 20, 21, 22, 23, 24, 25, 26, 27, 28, 29 and 30° C., to obtain compounds of formula (IV). In one embodiment of the present disclosure, the oxidizing agent is added and kept stirring for 1.5~2.5 hours, such as 1.5, 2, and 2.5 hours; and the reducing agent is added and kept stirring for 3.5~4.5 hours, such as 3.5, 4, and 4.5 hours. In one embodiment of the present disclosure, the deprotecting reagent is added and kept stirring for 3.5~4.5 hours, such as 3.5, 4, and 4.5 hours. In one embodiment of the present disclosure, the catalyst and oxidizing agent are added and kept stirring for 3.5~4.5 hours, such as 3.5, 4, and 4.5 hours.

Scheme 6

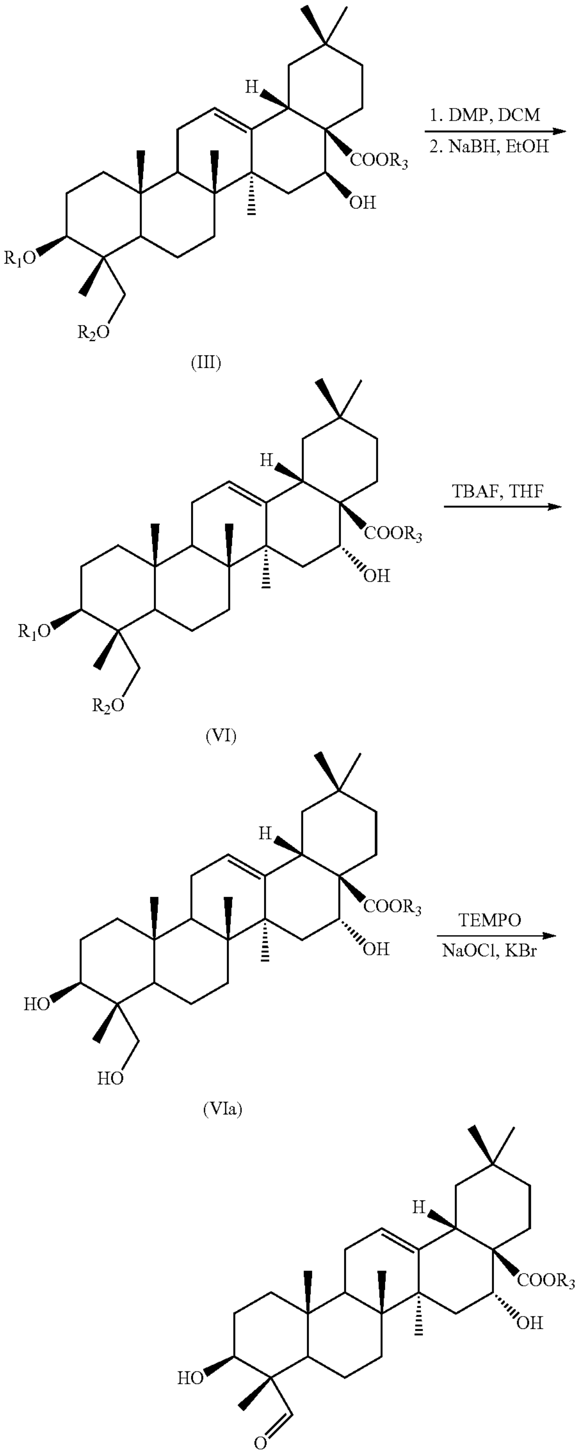

(III)

(VI)

(VIa)

(IV)

In one embodiment of the present disclosure, the compounds of formula (I) may be prepared with deprotecting reaction in accordance with Scheme 7. Compounds of formula (IV) are dissolved in a solvent, such as 1,4-dioxane, containing catalysts such as $Pd(OAc)_2$ and triphenylphosphine ($PPh_3$) for reaction. A protecting group scavenger such as piperidine is added to the reaction mixture and stirred at 15~30° C., such as 15, 16, 17, 18, 19, 20, 21, 22, 23, 24, 25, 26, 27, 28, 29 and 30° C., to obtain compounds of formula (I). In one embodiment of the present disclosure, the protecting group scavenger is added and kept stirring for 2.5~3.5 hours, such as 2.5, 3, and 3.5 hours.

Scheme 7

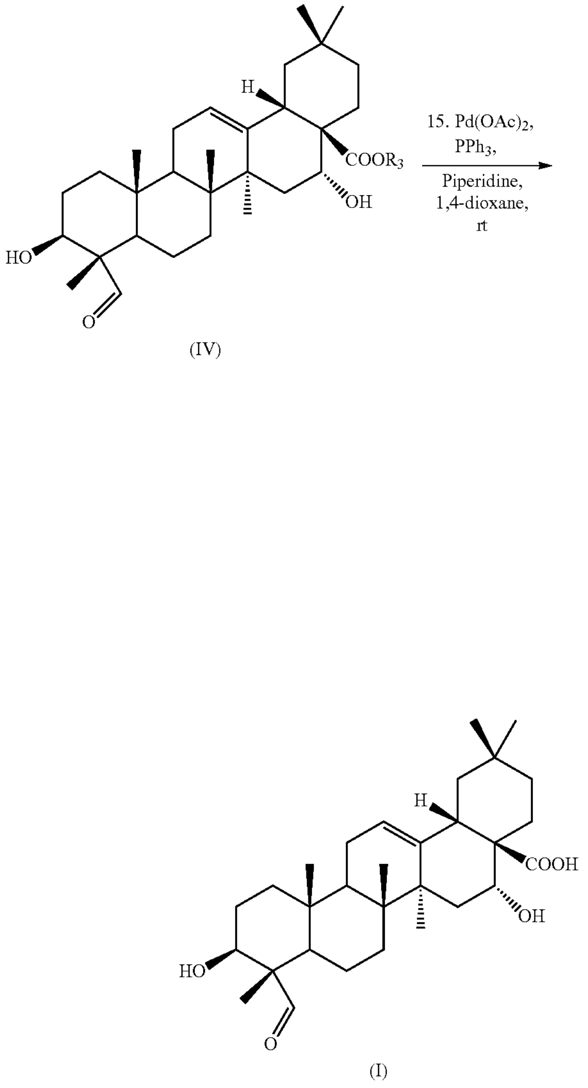

(IV)

(I)

In one embodiment of the present disclosure, further comprises a step of converting hederagenin into the compound of formula (XII) through attaching protecting groups on the hydroxyl groups of hederagenin in accordance with Scheme 8. Hederagenin and protecting group compound such as benzyl bromide (BnBr) are dissolved in a solvent, such as dimethylformamide (DMF), dichloromethane (DCM) or dimethyl sulfoxide (DMSO), containing a strong base such as NaH at −4~4° C., such as −4, −3, −2, −1, 0, 1, 2, 3 or 4° C. Then the mixture is stirred at 15~30° C., such as 15, 16, 17, 18, 19, 20, 21, 22, 23, 24, 25, 26, 27, 28, 29 and 30° C., to obtain compounds of formula (XII). In one embodiment of the present disclosure, the protecting group compound is added and kept stirring for 11~13 hours, such as 11, 12, and 13 hours.

Scheme 8

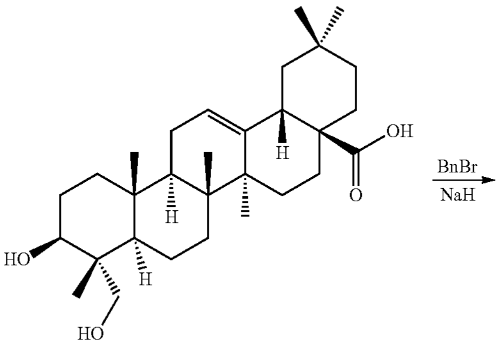

Hederagenin

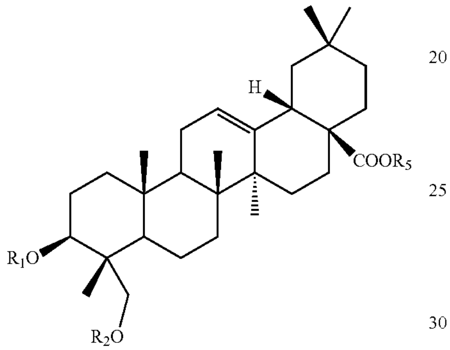

(XII)

In one embodiment of the present disclosure, further comprises a step of reducing a compound of formula (XII) to the compound of formula (XI) in accordance with Scheme 9. The compounds of formula (XII) are dissolved in a solvent such as THF, and then a reducing agent such as lithium aluminum hydride ($LiAlH_4$) is added at −4~4° C., such as −4, −3, −2, −1, 0, 1, 2, 3 or 4° C. The mixture is heated to 45~55° C. such as 45, 46, 47, 48, 49, 50, 51, 52, 53, 54 or 55° C. for complete reaction, and then cooled to −4~4° C. such as −4, −3, −2, −1, 0, 1, 2, 3 or 4° C., and a strong base such as sodium hydroxide (NaOH) is added to obtain compounds of formula (XI). In one embodiment of the present disclosure, the strong base is added and kept stirring for 14~16 minutes, such as 14, 15, and 16 minutes.

Scheme 9

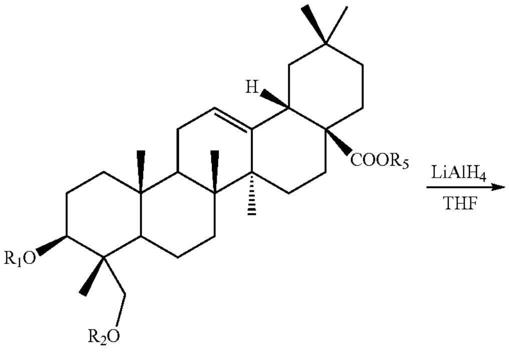

(XII)

-continued

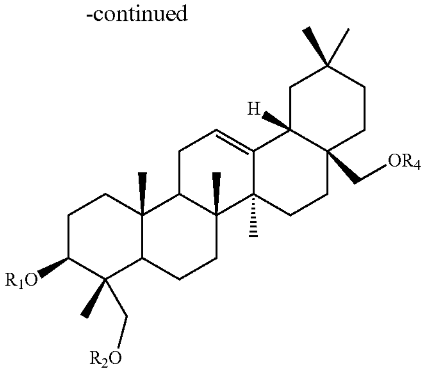

(XI)

In one embodiment of the present disclosure, further comprises a step of oxdizing a compound of formula (XI) into the compound of formula (VII) in accordance with Scheme 10. Compounds of formula (XI) are dissolved in solvent such as dimethylformamide (DMF), dichloromethane (DCM) or dimethyl sulfoxide (DMSO), and then an oxidizing agent such as Dess Martin periodinane (DMP) are added at 15~30° C., such as 15, 16, 17, 18, 19, 20, 21, 22, 23, 24, 25, 26, 27, 28, 29 and 30° C., to obtain the compound of formula (VII). In one embodiment of the present disclosure, the oxidizing agent is added and kept stirring for 1.5~2.5 hours, such as 1.5, 2, and 2.5 hours.

Scheme 10

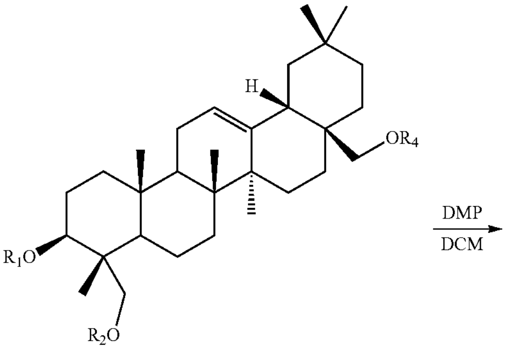

(XI)

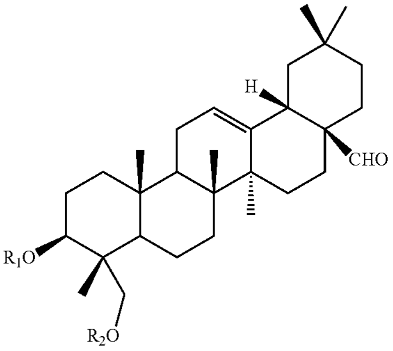

(VII)

The following examples are now exemplified to illustrate certain aspects of the present disclosure. These following examples are in no way to be considered to limit the scope of the present disclosure.

Figure 5:
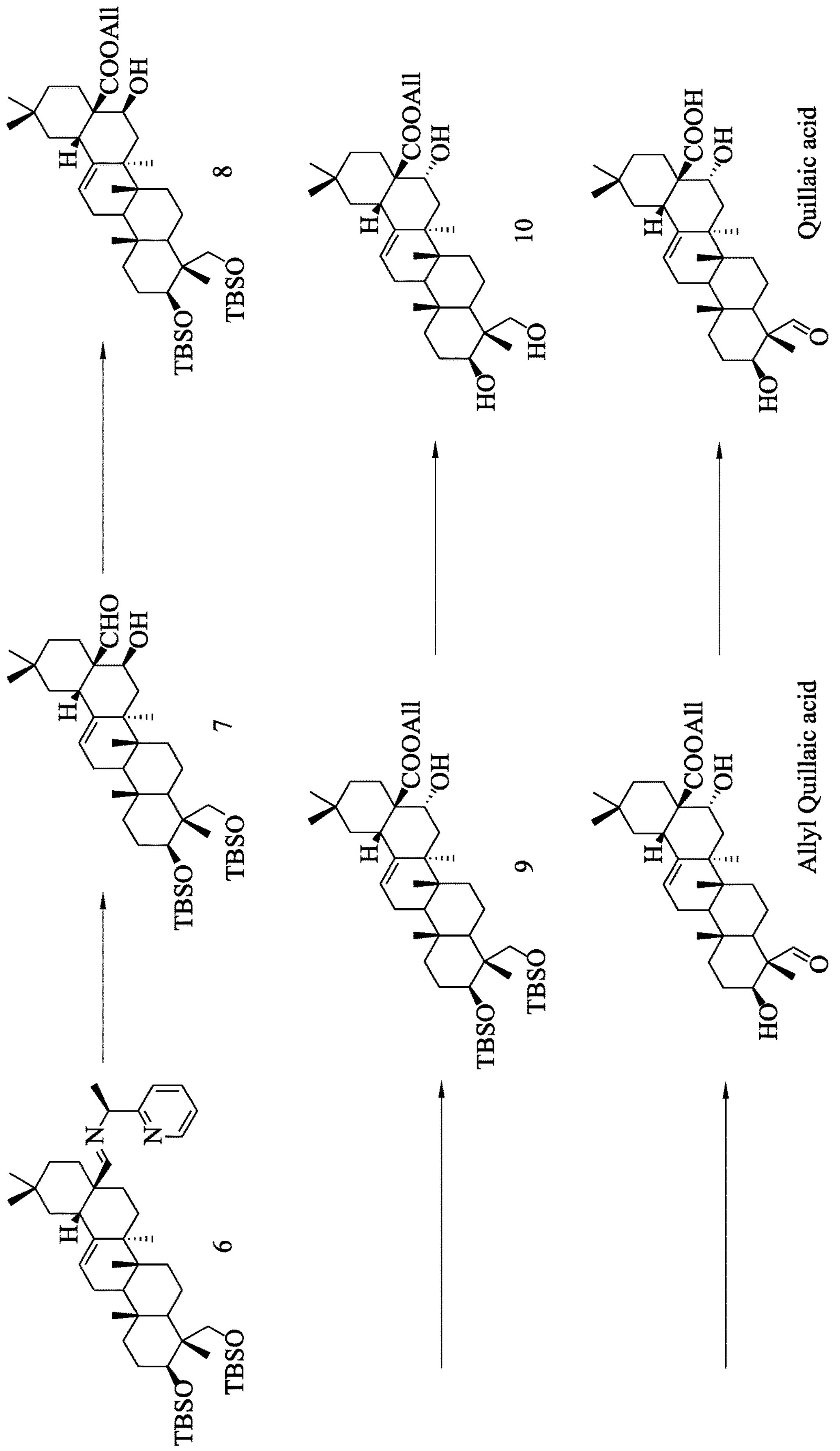
FIG. 5 shows a synthetic scheme of quillaic acid from compound 6 in accordance with one embodiment of the present disclosure.
Figure 6:
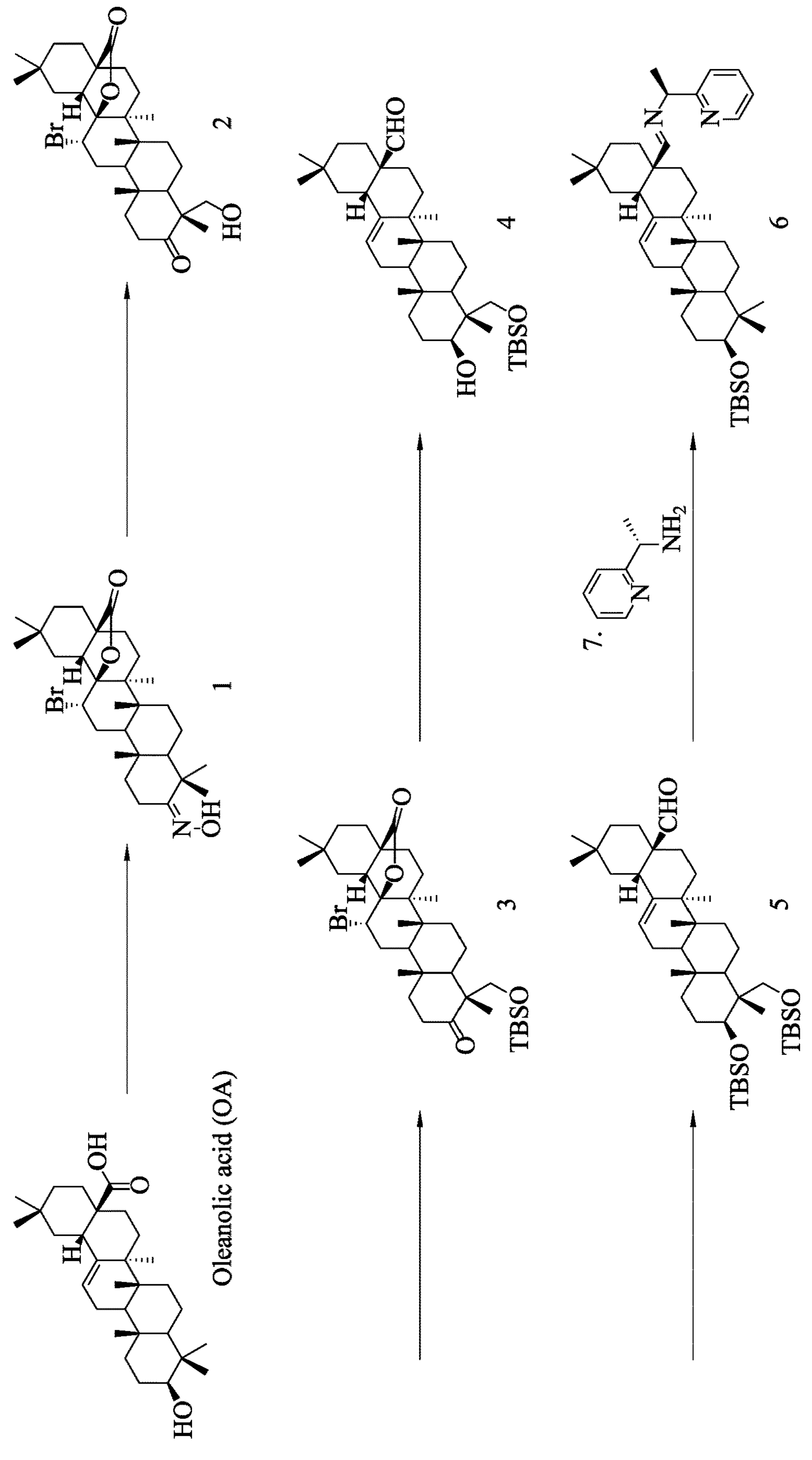
FIG. 6 shows a synthetic scheme of compound 6 from oleanolic acid in accordance with another embodiment of the present disclosure.
Figure 7:
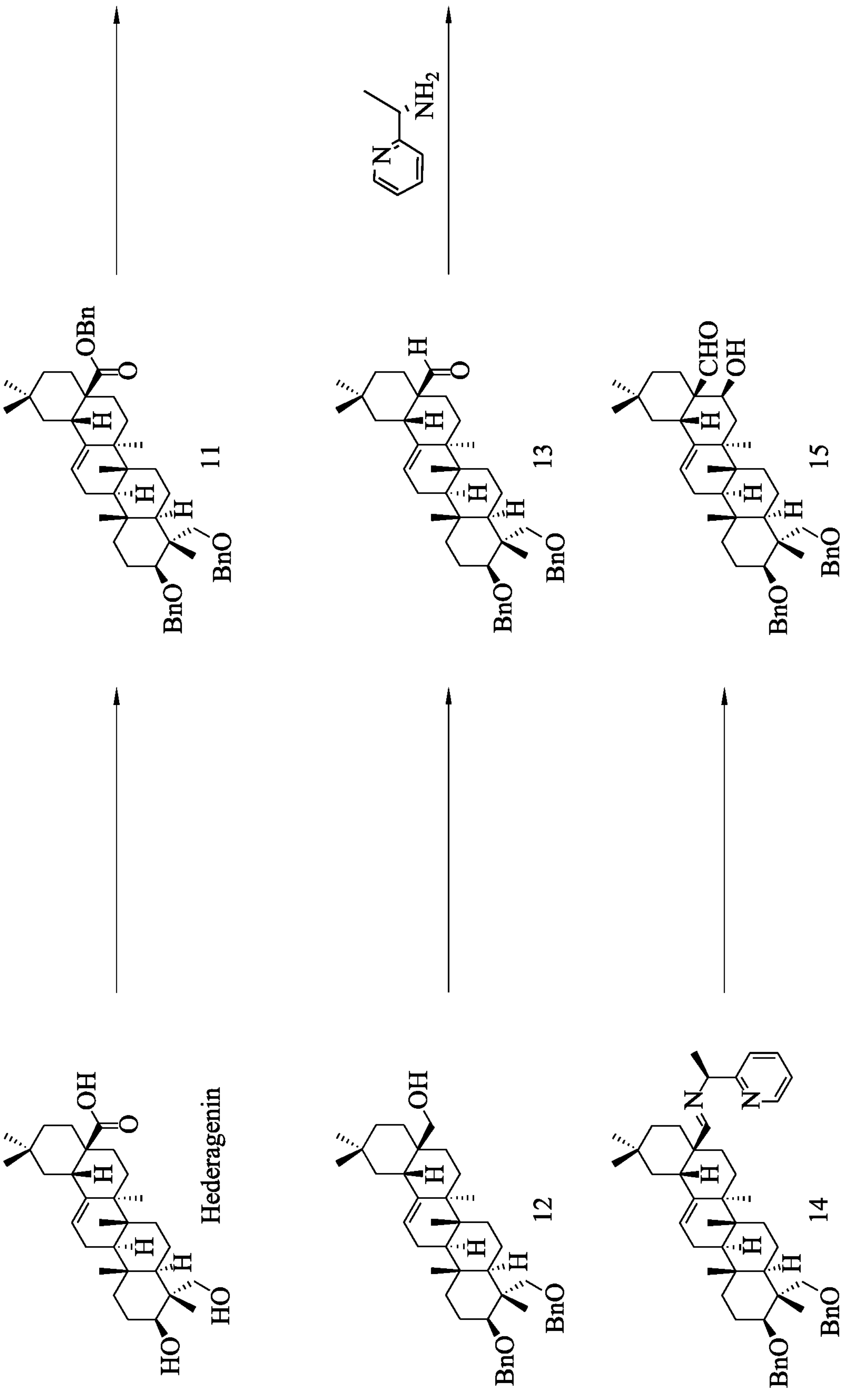
FIG. 7 shows a synthetic scheme of compound 15 from hederagenin in accordance with one embodiment of the present disclosure.

In the present examples, the preparation process of examples 1~6 can refer to the preparation scheme of FIG. 6; the preparation process of examples 7~12 can refer to the preparation scheme of FIG. 5; and the preparation process of examples 13~17 can refer to the preparation scheme of FIG. 7.

EXAMPLE 1: PREPARING OF THE COMPOUND 1

120 g oleanolic acid (OA) was added in to 1.2 L DCM and 275 mL pyridine. The solution turned to clear yellow solution with stirring in room temperature. 48 g NB S was added and kept stirring in room temperature for 1.5 hour. 48.8 g trichloroisocyanuric acid (TCCA) was added and kept stirring for 2 hours at room temperature. (caution: gas evolution). After full conversion, 32 mL IPA was added to the mixture and stirred for 1 hour at room temperature to quench excess TCCA. The mixture was added 58.2 g $HONH_2{\cdot}HCl$ and kept stirring at room temperature for 4 hours.

To remove excess reagent after the reaction, the mixture was diluted with 1200 mL DCM and extracted by 1M $HC_{14050}$ mL. The water later was back extracted by 1500 mL DCM. Later, the combined organic layer was washed by 0.5 M NaOH 4050 mL and brine 3000 mL. The organic layer was dried by magnesium sulfate anhydrous, filtrated and removed excess solvent in reduced pressure to obtain compound 1 as pale-yellow solid (132.1 g, 94.3% yield).

EXAMPLE 2: PREPARING OF THE COMPOUND 2

The pale-yellow solid compound 1 from the previous step (39.4 g) was dissolved in $Ac_2O$:AcOH=1:1 co-solvent (400 mL). After stirring for 90 min at 45° C., 2.5 g $Pd(OAc)_2$ and 35.7 g phenyliodine(III) diacetate was added sequentially and kept stirring for 8 hours at 45° C. Then, the solvent was removed in reduced pressure and the mixture was added THF:Acetone:1M HCl=1:1:1 co-solvent (600 mL) and stirred in 55° C. for 8 hours. After acid-catalyzed, the mixture was diluted by 650 mL ethyl acetate and extracted by water (650 mL) for three times. After drying with magnesium sulfate anhydrous and filtration, the organic layer was concentrated in reduced pressure and purified by column chromatography (Ethyl acetate:Hexanes=1:10) to obtain compound 2, as white foam (15.3 g, 37.7% yield). $^1H$ NMR (600 MHz, $CDCl_3$) δ 4.31 (dd, J=3.1, 2.4 Hz, 1H), 3.68 (d, J=11.3 Hz, 1H), 3.42 (d, J=11.3 Hz, 1H), 2.63 (ddd, J=17.9, 10.7, 7.2 Hz, 1H), 2.44 (ddd, J=15.1, 11.9, 3.7 Hz, 1H), 2.36 (ddd, J=16.4, 6.0, 2.8 Hz, 1H), 2.3 (d, J=9.5 Hz, 1H), 2.17 (td, J=13.4, 5.6 Hz, 1H), 2.01-1.93 (m, 5H), 1.91-1.86 15 (m, 4H), 1.77 (dd, J=5.8, 1.9 Hz, 1H), 1.65-1.63 (m, 3H), 1.59-1.50 (m, 2H), 1.45 (s, 3H), 1.44-1.41 (m, 1H), 1.36-1.32 (m, 2H), 1.28 (s, 3H), 1.26-1.24 (m, 1H), 1.08 (s, 3H), 1.00 (s, 6H), 0.9 (s, 3H) ppm; $^{13}C$ NMR (150 MHz, $CDCl_3$) δ 218.3, 178.8, 91.5, 66.8, 56.0, 52.5, 52.3, 48.6, 45.5, 44.8, 43.5, 42.4, 39.9, 38.6, 36.1, 35.1, 33.9, 33.8, 33.2, 31.9, 30.7, 29.1, 27.5, 23.5, 21.3, 21.0, 19.0, 18.5, 16.7, 16.6 ppm; HRMS (ESI-TOF) calci. for $C_{34145}$Br04[M+H]+ 549.2574, found 549.2574.

EXAMPLE 3: PREPARING OF THE COMPOUND 3

The white foam compound 2 (15.3 g) from the previous step was dissolved in DMF (60 mL) under $N_2$ atmosphere. Imidazole (5.7 g) and tert-butyldimethylsilyl chloride ($TBSC_1$, 10.6 g) was added sequentially in ice bath. The solution was stirred at room temperature for 4 hours. The mixture was diluted with ethyl acetate (750 mL) and quenched by adding $NaHCO_3$ (sat.) (950 mL) drop-wisely. And the water layer was extracted by ethyl acetate (750 mL) for two times. After drying with magnesium sulfate anhydrous and filtration, the organic layer was concentrated in reduced pressure and purified by column chromatography (Ethyl acetate:Hexanes=1:20) to obtain compound 3, as a white foam (15.9 g, 86.2% yield). $^1H$ NMR (600 MHz, $CDCl_3$) δ 4.32 (dd, J=3.7, 2.3 Hz, 1H), 3.68 (d, J=9.3 Hz, 1H), 3.42 (d, J=9.3 Hz, 1H), 2.52-2.50 (m, 1H), 2.45-2.34 (m, 2H), 2.36-2.34 (m, 1H), 2.20-2.14 (m, 2H), 2.05-1.93 (m, 5H), 1.91-1.86 (m, 2H), 1.66-1.56 (m, 6H), 1.52-1.47 (m, 1H), 1.46 (s, 3H), 1.37-1.28 (m, 5H), 1.27 (s, 3H), 1.26-1.24 (m, 1H), 0.99 (s, 3H), 0.91 (s, 3H), 0.90 (s, 3H), 0.89 (s, 9H), 0.04 (s, 3H), 0.01 (s, 3H) ppm; $^{13}C$ NMR (100 MHz, $CDCl_3$) δ 217.1, 178.7, 91.6, 68.6, 56.2, 52.4, 52.9, 45.8, 45.5, 44.2, 43.5, 42.1, 40.0, 37.3, 36.0, 35.6, 33.9, 33.6, 33.2, 31.9, 30.9, 29.1, 27.5, 25.8, 25.8, 25.8, 23.5, 21.3, 20.7, 19.0, 18.7, 18.2, 17.0, 16.5, -5.5, -5.8 ppm; HRMS (ESI-TOF) calci. for $C_{36}H_{59}BrO_4Si[M+H]^+$ 663.3439, found 663.3440.

EXAMPLE 4: PREPARING OF THE COMPOUND 4

Lithium tri-tert-butoxyaluminum hydride (1.72 g) in THF (30 mL) was added to compound 3 (1.76 g) from the previous step under $N_2$ atmosphere and stirred at room temperature. After 1 hour, the mixture was cooled to −78° C. and added diisobutylaluminum hydride (1.72 mL, 20 wt %) drop-wise and kept stirred for 90 min. Excess hydride was quenched by MeOH (3.5 mL) drop-wise before warming up to room temperature. AcOH (30 mL) and Zn powder (2.7 g) was added sequentially and the mixture was under sonification for 1 min. Then, stirred at 50° C. for 1 hour and cool to room temperature for 16 hours. The mixture was diluted with ethyl acetate 60 mL and extracted by water 50 mL for three times. After drying with magnesium sulfate anhydrous and filtration, the organic layer was concentrated in reduced pressure and purified by column chromatography (Ethyl acetate: Hexanes=1: 20) to obtain compound 4 as a white foam (1.2 g, 80.3%). $^1H$ NMR (600 MHz, $CDCl_3$) δ 9.39 (s, 1H), 5.34 (t, J=3.6 Hz, 1H), 3.7 (d, J=9.4 Hz, 1H), 3.59 (dd, J=11.1, 4.4 Hz, 1H), 3.35 (d, J=9.3 Hz, 1H), 2.62 (dd, J=13.7, 4.3 Hz, 1H), 1.97 (dt, J=13.8, 4.1 Hz, 1H), 1.89-1.87 (m, 2H), 1.70-1.60 (m, 5H), 1.58-1.51 (m, 3H), 1.48-1.38 (m, 3H), 1.33-1.22 (m, 6H), 1.20-1.17 (m, 2H), 1.12 (s, 3H), 1.07-1.04 (m, 1H), 1.01-0.95 (m, 2H), 0.94 (s, 3H), 0.913-0.910(m, 6H), 0.90 (s, 6H), 0.86 (s, 3H), 0.85-0.84 (m, 1H), 0.071 (s, 3H), 0.067 (s, 3H) ppm; $^{13}C$ NMR (100 MHz, $CDCl_3$) δ 207.5, 142.8, 123.3, 76.7, 73.2, 49.9, 49.1, 47.6, 45.6, 41.7, 41.6, 40.5, 39.5, 38.1, 36.8, 33.1, 33.1, 32.5, 30.6, 27.7, 26.7, 26.0, 25.8, 25.8, 25.8, 25.5, 23.4, 23.4, 22.1, 18.5, 18.1, 17.1, 15.5, 11.6, −5.7, −5.7 ppm; HRMS (ESI-TOF) calci. for $C_{36}H_{62}O_3Si$ $[M+H]^+$ 571.4541, found 571.4544.

EXAMPLE 5: PREPARING OF THE COMPOUND 5

Compound 4 (2.2 g) from the previous step was dissolved in DMF (12 mL) and DCM (12 mL) under $N_2$ atmosphere. Imidazole (0.67 g) and tert-butyldimethylsilyl chloride (TBSCl 1.16 g) was added sequentially in ice bath. The solution was stirred at room temperature for 4 hours. The mixture was diluted with ethyl acetate (120 mL) and quenched by adding $NaHCO_{3\ (sat.)}$ (150 mL) drop-wisely. And the water layer was extracted by ethyl acetate (120 mL) for two times. After drying with magnesium sulfate anhydrous and filtration, the organic layer was concentrated in reduced pressure and purified by column chromatography (Ethyl acetate: Hexanes=1:200) to obtain compound 5, as a white foam (2.5 g, yield=95.0%). $^1$H NMR (600 MHz, $CDCl_3$) δ 9.40 (s, 1H), 5.34 (s, 1H), 3.7 (dd, J=11.5, 4.7 Hz, 1H), 3.35 (d, J=9.6 Hz, 1H), 3.15 (d, J=9.6 Hz, 1H), 2.62 (dd, J=13.6, 4.1 Hz, 1H), 1.96 (dt, J=13.7, 4.0 Hz, 1H), 1.88-1.86 (m, 2H), 1.71-1.66 (m, 2H), 1.64-1.60 (m, 2H), 1.58-1.52 (m, 4H), 1.51-1.43 (m, 3H), 1.32-1.28 (m, 4H), 1.25-1.17 (m, 5H), 1.11 (s, 3H), 1.07-1.04 (m, 1H), 0.92-0.91(m, 8H), 0.90 (s, 9H), 0.86 (s, 9H), 0.73 (s, 3H), 0.57 (s, 3H), 0.03-0.02 (m, 12H) ppm; $^{13}$C NMR (100 MHz, $CDCl_3$) δ 207.7, 142.8, 123.4, 71.6, 63.9, 49.1, 47.6, 45.9, 45.6, 43.2, 41.8, 40.6, 39.5, 38.1, 36.4, 33.2, 33.0, 32.2, 30.6, 27.7, 27.2, 26.7, 26.0, 26.0, 26.0, 25.9, 25.9, 25.9, 25.3, 23.4, 23.4, 22.1, 18.1, 18.0, 17.9, 17.1, 15.6, 12.7, −3.7, −4.9, −5.3, −5.8 ppm; HRMS (ESI-TOF) calci. for $C_{42}H_{76}O_3Si_2$ $[M+H]^+$ 685.5406, found 685.5406.

EXAMPLE 6: PREPARING OF THE COMPOUND 6

Compound 5 (2.06 g) was put into round bottle under $N_2$ atmosphere. Dry toluene (30 ml) and (S)-1-pyridin-2-yl-ethylamine (0.73 g) were added sequentially. Then, the reaction was warmed to 80° C. and stirred for 2 hours. The excess solvents were removed by vacuum to afford compound 6 without further purification.

EXAMPLE 7: PREPARING OF THE COMPOUND 7

The $Cu(OTf)_2$ (1.4. g) and Na ascorbate (1.19 g) were added to the mixture of compound 6 from the previous step. Methanol (15 ml) and acetone (15 ml) were also added to the mixture and stirred at room temperature. The $O_2$ balloon was made to bubble through the mixture for 30 minutes. Then, the mixture was warmed to 50° C. and stirred for 120 mins. After the reaction, 30 ml ethyl acetate with sat. aq. $Na_4$EDTA solution (30 mL) were added and stirred for 1 hour. The layers were separated and the aqueous layer was extracted with ethyl acetate (30 mL) three times. The combined organic layers were washed with brine (30 mL), dried over magnesium sulfate anhydrous and filtration, and concentrated under vacuum. The crude product was purified by silica gel flash chromatography (ethyl acetate:hexanes=1:40) to obtain compound 7 (1.1 g, yield=51.8%) as a white solid. $^1$H NMR (400 MHz, $CDCl_3$) δ 9.46 (s, 1H), 5.39 (s, 1H), 4.16 (d, J=11.8 Hz, 1H), 3.68 (d, J=7.8 Hz, 1H), 3.35 (d, J=9.6 Hz, 1H), 3.14 (d, J=9.5 Hz, 1H), 2.70 (d, J=10.3 Hz, 1H), 1.97-1.94 (m, 1H), 1.86-1.79 (m, 3H), 1.61-1.50 (m, 11H), 1.37-1.27 (m, 6H), 1.17 (s, 3H), 0.95 (s, 3H), 0.91 (s, 6H), 0.89 (s, 9H), 0.85 (s, 9H), 0.76 (s, 3H), 0.57 (s, 3H), 0.02 (s, 12H) ppm; $^{13}$C NMR (100 MHz, $CDCl_3$) δ 210.0, 141.7, 124.2, 71.6, 65.7, 63.9, 52.5, 46.7, 45.9, 45.3, 43.9, 43.3, 43.2, 39.7, 38.2, 36.7, 36.3, 33.1, 32.4, 32.1, 30.4, 27.2, 26.4, 26.0, 26.0, 26.0, 25.9, 25.9, 25.9, 23.5, 23.5, 21.7, 18.1, 18.0, 17.8, 17.2, 15.6, 12.7, -3.7, -4.9, -5.3, -5.9 ppm; HRMS (ESI-TOF) calci. for $C_{42}H_{76}O_4Si_2$ $[M+H]^+$ 701.5355, found 701.5354.

EXAMPLE 8: PREPARING OF THE COMPOUND 8

Compound 7 (7.55 g) dissolved in DMSO (21.6 mL) and tert-Butanol (99.2 mL), was added with a solution of $NaClO_2$(6.96 g) and $NaH_2PO_4 \cdot H_2O$ (9.24 mg) in water (51.8 mL). The reaction was stirred at room temperature for 4 hours. The mixture was diluted with an aqueous 10% NaOH solution (to pH=9) and the aqueous phase was extracted with hexanes. The aqueous phase was then acidified with aqueous 1N HCl solution (to pH=1), and extracted with DCM (200 mL). The combined DCM layers were washed with brine (200 mL), dried over magnesium sulfate anhydrous and filtration, and concentrated under vacuum to obtain a crude mixture without further purification.

The crude mixture from the previous step was dissolved in THF/$H_2$=10/1 (330 mL), allyl bromide (1.9 mL, 22.0 mmol), tetra-n-butylammonium iodide (162.5 mg, 0.44 mmol) and $K_2CO_3$ (3.0 g, 22.0 mmol) was added subsequently. The reaction was stirred at 65° C. for 4 hours. THF was removed by vacuum. After diluting the mixture with ethyl acetate (300 mL), the layers were separated and the aqueous layer was extracted with ethyl acetate (100 mL) two times. The combined organic layers were washed with brine (200 mL), dried over magnesium sulfate anhydrous and filtration, and concentrated under vacuum. The crude product was purified by silica gel flash chromatography (ethyl acetate:hexanes=1:40) to obtain compound 8 (5.5 g, yield=66.4%, 2 steps) as a white solid. $^1$H NMR (400 MHz, $CDCl_3$) δ 6.90 (ddd, J=15.0, 7.1, 3.7 Hz, 1H), 5.38-5.25 (m, 3H), 4.56 (ddd, J=19.2, 8.9, 3.8, Hz, 2H), 4.17 (dd, J=5.3, 2.8 Hz, 1H), 3.70 (dd, J=7.5, 3.1 Hz, 1H), 3.37 (d, J=6.5 Hz, 1H), 3.16 (d, J=6.4 Hz, 1H), 3.04 (dd, J=9.2, 2.2 Hz, 1H), 2.27 (d, J=8.5 Hz, 1H), 1.88 (dd, J=5.8, 2.1 Hz, 2H), 1.71-1.62 (m, 5H), 1.56-1.50 (m, 7H), 1.30-1.27 (m, 6H), 1.19 (s, 3H), 0.97 (s, 3H), 0.93 (s, 6H), 0.92 (s, 9H), 0.88 (s, 9H), 0.74 (s, 3H), 0.59 (s, 3H), 0.04 (s, 12H) ppm; $^{13}$C NMR (100 MHz, $CDCl_3$) δ 177.9, 142.3, 131.8, 123.1, 118.4, 71.6, 65.1, 64.8, 63.9, 50.6, 46.8, 46.0, 45.5, 44.0, 43.3, 43.2, 39.4, 38.1, 37.4, 36.4, 33.3, 33.0, 32.1, 30.5, 27.2, 26.7, 26.7, 26.0, 26.0, 26.0, 25.9, 25.9, 25.9, 23.9, 23.5, 18.1, 18.0, 17.9, 17.0, 15.6, 12.7, -3.7, -4.9, -5.3, -5.9 ppm; HRMS (ESI-TOF) calci. for $C_{45}H_{80}O_5Si_2$ $[M+H]^+$ 757.5617, found 757.5621.

EXAMPLE 9: PREPARING OF THE COMPOUND 9

Compound 8 (5.5 g) dissolved in DCM (73.0 mL), was added Dess Martin periodinane (12.4 g) and $NaHCO_3$ (1.84 g). After stirring at 25° C. for 2 hours, the excess reagents were quenched with saturated aq. $Na_2SO_3$ (100 mL), and the resulting mixture was extracted with ethyl acetate (100 mL) for three times. The combined organic phases were washed with brine (100 mL), dried over magnesium sulfate anhydrous and filtration, and concentrated under vacuum to obtain a white foam compound without further purification.

The white foam compound from the previous step was dissolved in ethanol (73 mL) and was added sodium borohydride (2.8 g). The reaction was stirred at room temperature for 4 hours. The reaction was quenched with $H_2O$ (100 mL), then the ethanol was removed by vacuum. After diluting the mixture with DCM (100 mL), the layers were separated and the aqueous layer was extracted with DCM (100 mL) for three times. The combined organic layers were washed with brine (100 mL), dried over magnesium sulfate anhydrous and filtration, and concentrated under vacuum. The residue was purified by flash column chromatography (ethyl acetate: hexanes=1:40) to obtain compound 9 (3.4 g, yield=2 steps 60.4%) as a white foam. $^1$H NMR (600 MHz, $CDCl_3$) δ 5.90-5.83 (m, 1H, All internal alkenyl CH), 5.40 (t, J=3.6 Hz, 1H), 5.30 (ddd, J=17.0, 4.5 Hz, 1H), 5.21 (ddd, J=10.6, 3.8 Hz, 1H), 4.54-4.46 (m, 3H), 3.70 (dd, J=11.4, 4.8 Hz, 1H), 3.35 (d, J=9.7 Hz, 1H), 3.15 (d, J=9.6 Hz, 1H), 3.07 (dd, J=14.4, 4.4 Hz, 1H), 2.18-2.13 (m, 1H), 1.90-1.87 (m, 3H), 1.85-1.81 (m, 1H), 1.79-1.72 (m, 2H), 1.62-1.61 (m, 1H), 1.59-1.57 (m, 3H), 1.53-1.51 (m, 2H), 1.37 (dd, J=15.1, 3.8 Hz, 1H), 1.32 (s, 3H), 1.29-1.28 (m, 1H), 1.26-1.25 (m, 3H), 1.21-1.11 (m, 3H), 0.97 (s, 3H), 0.93 (s, 3H), 0.90 (s, 12H), 0.86 (s, 9H), 0.73 (s, 3H), 0.57 (s, 3H), 0.03 —0.02 (m, 12H) ppm; $^{13}$C NMR (100 MHz, $CDCl_3$) δ 176.5, 142.5, 132.2, 123.2, 118.0, 75.1, 71.6, 65.1, 63.9, 48.9, 46.8, 46.4, 46.0, 43.2, 41.5, 40.8, 39.6, 38.1, 36.5, 35.5, 35.5, 32.8, 32.4, 30.6, 30.4, 27.2, 26.9, 26.0, 26.0, 26.0, 25.9, 25.9, 25.9, 24.6, 23.4, 18.1, 18.0, 17.9, 17.2, 15.8, 12.6, −3.7, −4.9, −5.3, −5.8 ppm; HRMS (ESI-TOF) calci. for $C_{45}H_{80}O_5Si_2$ $[M+H]^+$ 757.5617, found 757.5621.

EXAMPLE 10: PREPARING OF THE COMPOUND 10

Compound 9 (2.3 g) dissolved in THF (60 mL), was added TBAF (7.8 g, 1M solution in THF). The reaction was stirred at 50° C. for 4 hours. The THF was removed by vacuum. After diluting the mixture with DCM (80 mL), the layers were separated and the aqueous layer was extracted with DCM (80 mL) for three times. The combined organic layers were washed with brine (80 mL), dried over magnesium sulfate anhydrous and filtration, and concentrated under vacuum. The residue was purified by flash column chromatography 9 (ethyl acetate: hexanes=1:4) to obtain compound 10 (1.32 g, yield=83.3%) as a white foam. $^1$H NMR (600 MHz, $CDCl_3$) δ 5.90-5.84 (m, 1H, All internal alkenyl CH), 5.39 (t, J=3.5 Hz, 1H), 5.30 (ddd, J=17.1, 4.4 Hz, 1H), 5.21 (ddd, J=10.6, 3.8 Hz, 1H), 4.54-4.46 (m, 3H), 3.73 (d, J=10.3 Hz, 1H), 3.64 (dd, J=9.1, 7.0 Hz, 1H), 3.44 (d, J=10.3 Hz, 1H), 3.07 (dd, J=14.5, 4.4 Hz, 1H), 2.17-2.13 (m, 1H), 1.90-1.88 (m, 3H), 1.83-1.81 (m, 3H), 1.79-1.75 (m, 6H), 1.65-1.60 (m, 4H), 1.50-1.46 (m, 1H), 1.37-1.35 (m, 4H), 1.27-1.25 (m, 4H), 1.14-1.11 (m, 1H), 0.97 (s, 3H), 0.96 (s, 3H), 0.90 (s, 3H), 0.89 (s, 3H), 0.73 (s, 3H) ppm; $^{13}$C NMR (100 MHz, $CDCl_3$) δ 176.4, 142.7, 132.2, 122.8, 118.1, 74.9, 72.1, 65.2, 49.9, 48.8, 46.7, 46.3, 41.8, 41.2, 40.6, 39.5, 38.2, 36.9, 35.5, 32.8, 32.7, 30.6, 30.4, 29.7, 29.7, 27.0, 26.8, 24.7, 23.3, 18.4, 17.1, 15.8, 11.4 ppm; HRMS (ESI-TOF) calci. for $C_{33}H_{52}O_5$ $[M+H]^+$ 529.3888, found 529.3887.

EXAMPLE 11: PREPARING OF THE ALLYL QUILLAIC ACID

Compound 10 (1.0 g) dissolved in DCM (20 mL), was added TEMPO (1.48 g) and KBr (22.3 mg). Then a solution of NaOCl (848.6 mg) in 5% aqueous $NaHCO_3$ (0.035 M) was added. The reaction was stirred vigorously at room temperature for 4 hours. Diluted the mixture with DCM (30 mL). The organic layers were washed with $H_2O$ (30 mL), brine (30 mL), dried over magnesium sulfate anhydrous and filtration, and concentrated under vacuum. The residue was purified by flash column chromatography (ethyl acetate: hexanes=1:4) to obtain Allyl Quillaic acid (831.7 mg, yield=83.1%) as a white foam. $^1$H NMR (600 MHz, $CDCl_3$) δ 9.41 (s, 1H, H-23), 5.90-5.83 (m, 1H, All internal alkenyl CH), 5.36 (d, J=3.5, 1H, H-12), 5.27 (dd, J=17.2, 1.2 Hz, 1H, All terminal alkenyl $CH_a$), 5.21 (d, J=10.4 Hz, 1H, All terminal alkenyl $CH_b$), 4.55-4.46 (m, 3H, H-16, allylic $CH_2$), 3.77 (dd, J=11.2, 4.6 Hz, 1H, H-3), 3.08 (dd, J=14.4, 4.3 Hz, 1H, H-18), 2.17 (t, J=13.7 Hz, 1H, H-19), 1.93-1.89 (m, 3H), 1.83-1.65 (m, 8H), 1.54-1.48 (m, 6H), 1.38 (s, 3H), 1.36-1.27 (m, 4H), 1.22-1.20 (m, 1H), 1.13 (dd, J=12.9, 4.1, 1H), 1.07 (s, 3H), 1.05-0.99 (m, 3H), 0.98 (s, 6H), 0.91 (s, 3H), 0.74 (s, 3H); $^{13}$C NMR (150 MHz, $CDCl_3$) δ 207.0 (C-23), 176.3 (C-28), 142.8, 132.1, 122.5, 118.1, 74.9, 71.8, 65.2, 55.2, 48.7, 48.2, 46.6, 46.4, 41.4, 40.6, 39.9, 38.1, 36.0, 35.5, 35.4, 32.8, 32.3, 30.7, 30.4, 27.0, 26.1, 24.6, 23.3, 20.7, 17.0, 15.7, 8.9 ppm; HRMS (ESI-TOF) calci for $C_{33}H_{51}O_5$ $[M+H]^+$527.3731, found 527.3733.

EXAMPLE 12: PREPARING OF QUILLAIC ACID

Allyl Quillaic acid (800 mg) was dissolved in 1,4-dioxane (20 mL). The mixture of $Pd(OAc)_2$ (34 mg) and triphenylphosphine (0.2 g) dissolved in 1,4-dioxane (13 mL) was added Allyl Quillaic acid solution for reaction. Piperidine (260 mg) was added to the 20 reaction mixture and stirred at room temperature for 3 hours. The mixture was concentrated to dryness under vacuum. The residue was purified by column chromatography (ethyl acetate:hexanes=1:15) to obtain Quillaic acid (502.7 mg, yield=68%) as a white foam. $^1$H NMR (600 MHz, Methanol-d4) 6 9.30 (s, 1H, H-23), 5.30(1H, alkenyl CH), 4.46 (1H, —OH), 3.77 (1H, H-3), 3.00 (1H), 2.30 (t, 1H), 1.98-1.67 (m, 11H), 1.61-1.47 (m, 2H), 1.40(s, 3H), 1.32-1.35 (m, 2H), 1.28-1.25 (m, 1H), 1.16-1.12 (m, 2H), 1.02-0.97 (m, 11H), 0.91-0.88 (m, 4H), 0.80 (s, 3H); $^{13}$C NMR (150 MHz, Methanol-$d_4$) 6 208.7 (C-23), 181.2 (C-28), 145.3, 123.3, 75.4, 72.9, 56.9, 49.7, 48.9, 48.2, 47.8, 42.9, 42.2, 41.1, 39.6, 37.1, 36.7, 36.3, 33.7, 33.6, 32.9, 31.6, 27.4, 27.1, 25.0, 24.6, 21.9, 17.9, 16.3, 9.5 ppm

EXAMPLE 13: PREPARING OF THE COMPOUND 11

To a stirred solution of hederagenin (6.00 g, 12.6 mmol) and BnBr (14.8 mL, 124.7 mmol) in dry DMF (20.0 mL) was added NaH (60 wt %, dispersed in mineral oil, 2.3 g, 94.5 mmol) portion-wise at 0° C. After the addition was completed, the stirring was continued at room temperature under $N_2$ atmosphere for another 12 h before ethyl acetate (20.0 mL) was added to dilute the reaction mixture. The resulting mixture was thoroughly washed with water (2×20 mL) and brine (20 mL), and the organic layer was then dried over anhydrous $MgSO_4$, filtered, and concentrated under vacuum. The residue was purified by flash column chromatography (EtOAc/Hexane=1:100) to obtain compound 11 as a white foam (6.9 g, 73.8% yield).

EXAMPLE 14: PREPARING OF THE COMPOUND 12

A solution of compound 11 (6.0 g, 8.0 mmol) in dry THF (10 mL) was added slowly to a solution of lithium aluminum hydride (0.929 g, 24.0 mmol) in dry THF (10 mL) at 0° C. The solution was heated to 50° C. After the reaction was completed, the mixture was cooled to 0° C. and excess $LiAlH_4$ was deactivated by adding water (10 mL). An aqueous solution of 1 N sodium hydroxide (10 mL) was added, and the mixture was stirred for 15 min. The solid was filtered off, washed with ethyl acetate (2×20 mL), and the organic phase was washed with water (2×20 mL) and brine (20 mL). The combined organic phases were dried over $MgSO_4$ and concentrated under reduced pressure. After column chromatography (Hexane/EtOAc=20:1) compound 12 was obtained as a white foam (3.28 g, 64.2% yield).

EXAMPLE 15: PREPARING OF THE COMPOUND 13

To a stirred solution of compound 12 (2.0 g, 3.1 mmol) in $CH_2Cl_2$ (4.0 mL), was 5 added Dess Martin periodinane (2.63 g, 6.2 mmol). After stirring at 25° C. for 2 hours, the excess reagents were quenched with saturated aq. $Na_2SO_3$ (5.0 mL), and the resulting mixture was extracted with EtOAc (3×5.0 mL). The combined organic phases were washed with brine (4.0 mL), dried over anhydrous $MgSO_4$, filtered, and concentrated under vacuum. The residue was purified by flash column chromatography (EtOAc/Hexane=1:50) to obtain compound 13 as a white foam (1.3 g, 63% yield). $^1$H NMR (600 MHz, $CDCl_3$) δ 9.39 (s, 1H, H-28), 7.30-7.20 (10H, Ar—H) 5.33(t, 1H, alkenyl CH), 4.60-4.29 (4H, —$CH_2$) 3.50 (dd, 1H), 3.37 (1H), 3.08 (1H), 2.62 (dd, 1H), 1.89-1.85 (m, 2H), 1.70-1.50 (9H), 1.47-1.36 (3H), 1.30-1.20 (8H), 1.14 (s, 3H, $CH_3$), 0.92 (s, 3H, $CH_3$), 0.91(s, 3H, $CH_3$), 0.90 (s, 3H, $CH_3$), 0.71 (s, 3H, $CH_3$), 0.68 (s, 3H, $CH_3$).

EXAMPLE 16: PREPARING OF THE COMPOUND 14

To a solution of compound 13 (100 mg, 0.16 mmol) and p-toluenesulfonic acid monohydrate (2.8 mg, 0.016 mmol) in toluene (2 mL) in a flame-dried flask, was added amine (S)-1-pyridin-2-yl-ethylamine (28.8 μL, 0.48 mmol). The mixture was heated to 80° C. until imine formation was complete as monitored by TLC. The mixture was cooled to 25° C. and concentrated under vacuum to obtain compound 14.

EXAMPLE 17: PREPARING OF THE COMPOUND 15

Copper(II) nitrate trihydrate (77.2 mg, 0.32 mmol) and the obtained crude imine 14 were added to a reaction flask followed by THF, acetone and MeOH (3 mL, 1:1:1) at room temperature. The mixture was stirred vigorously for 1 hour. Hydrogen peroxide (18.8 μL, 35 wt % in $H_2O$, 0.8 mmol) was then added to the reaction mixture dropwise, which resulted in the disappearance of the precipitate and gave a blue green solution. The reaction mixture was then allowed to stir for 24 hours at room temperature. Then, sat. aq. $Na_4$EDTA solution (3.0 mL) was added and the mixture was stirred for 1 h. The layers were separated and the aqueous layer was extracted with ethyl acetate (2×5 mL). The combined organic layers were washed with brine (2×5 mL), dried over anhydrous $MgSO_4$, and concentrated under vacuum. The crude product was purified by silica gel flash chromatography (EtOAc/Hexane=1:20) to obtain compound 15 as a white foam (32 mg, 30% yield). $^1$H NMR (600 MHz, $CDCl_3$) δ 9.50 (1H, H-28), 7.34-7.28 (10H, Ar—H) 5.43(t, 1H, alkenyl CH), 4.65-4.33 (4H, —$CH_2$), 4.21 (m, 1H, —CH—OH) 3.54 (dd, 1H), 3.41 (d, 1H), 3.13 (d, 1H), 2.74 (dd, 1H), 2.02-1.81 (6H), 1.68-1.54 (8H), 1.46-1.40 (3H), 1.36-1.32 (4H), 1.25 (s, 3H, $CH_3$), 0.99 (s, 3H, $CH_3$), 0.98(s, 3H, $CH_3$), 0.97 (s, 3H, $CH_3$), 0.79 (s, 3H, $CH_3$), 0.72 (s, 3H, $CH_3$).

Although the present disclosure has been described in considerable detail with reference to certain embodiments thereof, other embodiments are possible. Therefore, the scope of the claims and the scope of the claims are not limited to the description contained in the embodiments herein.

It will be apparent to those skilled in the art that various modifications and variations can be made to the structure of the present disclosure without departing from the scope of the present disclosure. In view of the foregoing, it is intended that the present disclosure cover modifications and variations of this disclosure provided they fall within the scope of the following claims.

What is claimed is:

1. A method of preparing a triterpenoid compound of formula (I), comprising:

formula (I)

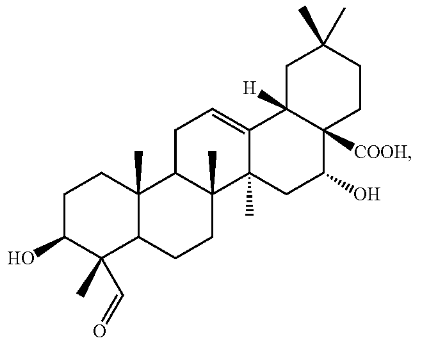

a step of converting a compound of formula (II) into a compound of formula (III) through sequentially oxidizing an aldehyde group of formula (II) to a carboxyl group by oxidation, and forming an oxygen protecting group on one oxygen atom of the carboxyl group by attaching a protecting group, a step of converting the compound of formula (III) into a compound of formula (IV) through epimerization, deprotection and oxidation sequentially, and a step of converting the compound of formula (IV) into the compound of formula (I) with deprotecting reaction, formula (II)

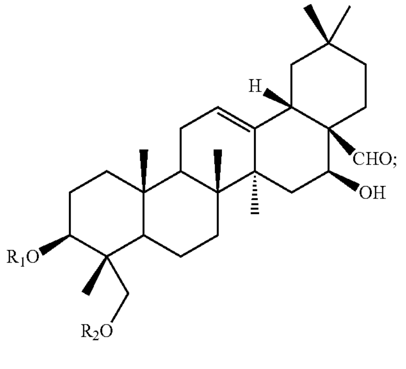

-continued formula (III)

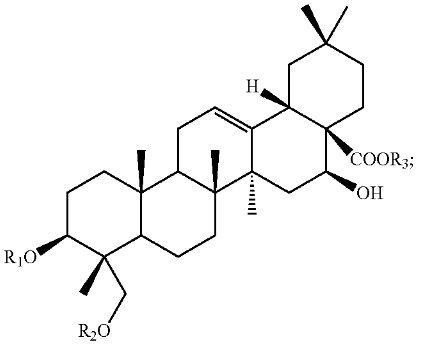

formula (IV)

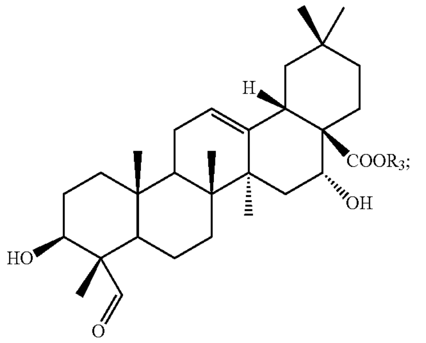

wherein $R_1$ and $R_2$ independently represent hydrogen or a protecting group selected from the group consisting of $C_1$-$C_8$ alkyl, allyl, $C_2$-$C_8$ alkenyl, $C_2$-$C_8$ alkynyl, ($C_6$-$C_{12}$)aryl($C_1$-$C_8$)alkyl, tri($C_1$-$C_8$)alkylsilyl, di($C_1$-$C_8$) alkyl($C_6$-$C_{12}$)arylsilyl, di($C_6$-$C_{12}$)aryl($C_1$-$C_8$)alkylsilyl, tri($C_6$-$C_{12}$)arylsilyl, —C(O)$R_7$, and —C(O)O$R_8$, and each of which is substituted with from 0 to 4 substituents independently selected from the group consisting of hydroxy, cyano, halo, halo($C_1$-$C_6$) alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy, wherein $R_7$ and $R_8$ are independently $C_1$-$C_8$ alkyl or $C_6$-$C_{12}$ aryl, wherein R3 is a protecting group selected from the group consisting of C1-C8 alkyl, C2-C8alkenyl, C2-C8 alkynyl, (C6-C12)aryl(C1-C8)alkyl, C6-C12 arylacyl, tri (C1-C8)alkylsilyl, di(C1-C8)alkyl(C6-C12)arylsilyl, di(C6-C12)aryl(C1-C8)alkylsilyl and tri(C6-C12)arylsilyl, and each of which is substituted with from 0 to 4 substituents independently selected from the group consisting of hydroxy, cyano, halo, halo(C1-C6)alkyl, halo(C1-C6)alkyloxy, (C1-C6)alkylthio, C1-C6 alkyl, C2-C6 alkenyl, C2-C6 alkynyl, C3-C7 cycloalkyl and C1-C6 alkoxy.

2. The method of claim 1, further comprising a step of subjecting the compound of formula (III) to epimerization at the carbon position where a hydroxyl group is attached to form a compound of formula (VI), and a step of converting the compound of formula (VI) to a compound of formula (IV) with deprotection and oxidation sequentially, formula (III)

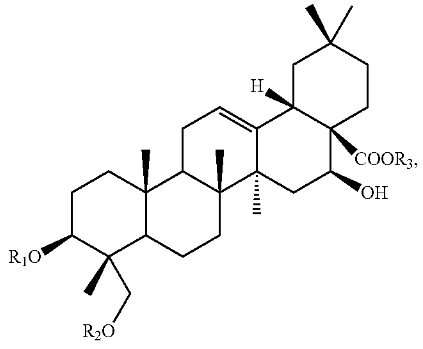

formula (VI)

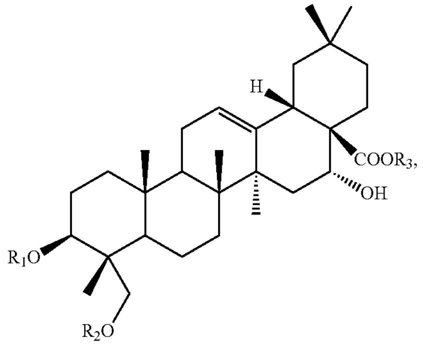

formula (IV)

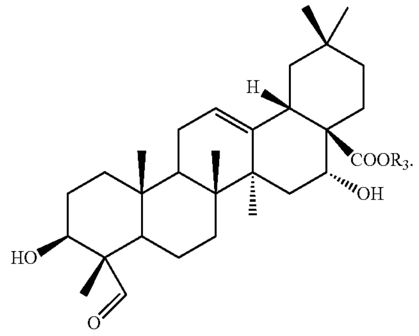

3. The method of claim 1, further comprising a step of converting a compound of formula (VII) into the compound of formula (II) through directing group introduction and C—H activation sequentially, formula (VII)

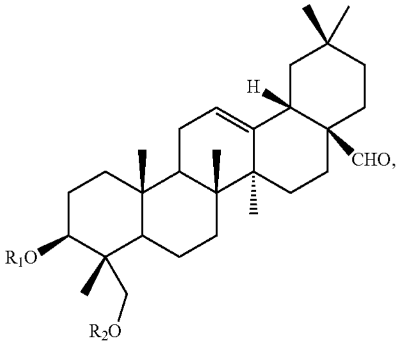

-continued formula (II)

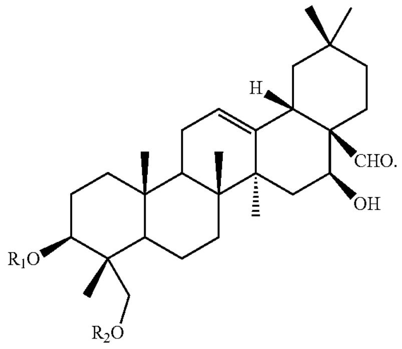

4. The method of claim 3, further comprising a step of converting the compound of formula (VII) into a compound of formula (VIII) by reacting the compound of formula (VII) with a compound of formula (a) through directing group introduction, and a step of converting the compound of formula (VIII) into the compound of formula (II) with C—H activation, formula (VII)

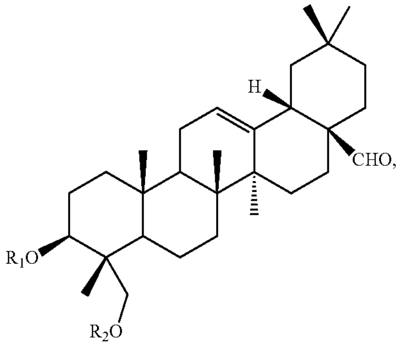

formula (VIII)

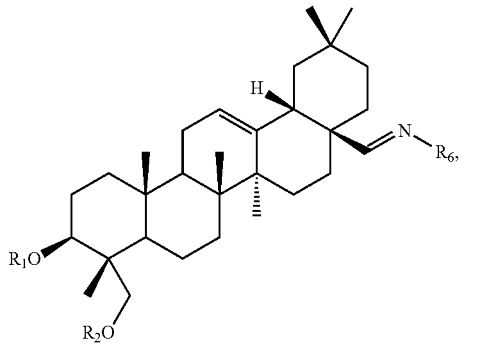

-continued formula (II)

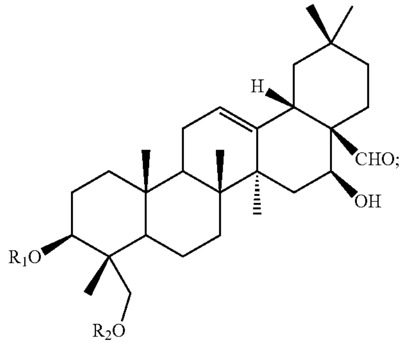

wherein $R_6$ represents

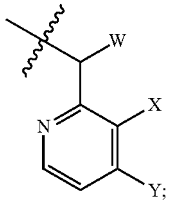

W is H or $C_1$-$C_8$ alkyl group and X and Y independently represent hydrogen, hydroxy, cyano, halo, $C_6$-$C_{12}$ aryl or $C_5$-$C_{12}$ heteroaryl, and wherein the compound of formula (a) represents

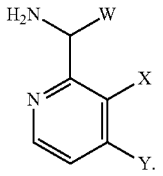

5. The method of claim 3, further comprising a step of converting oleanolic acid to the compound of formula (VII) through halolactone oxime formation, C—H activation, attaching protecting group and reduction sequentially, formula (VII)

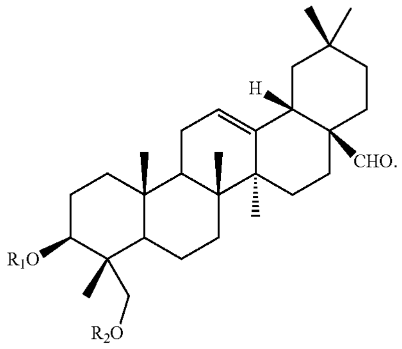

6. The method of claim 4, wherein the compound of formula (VII) is obtained by converting a compound of formula (IX) into the compound of formula (VII) through reduction and optionally attaching protecting group sequentially, formula (IX)

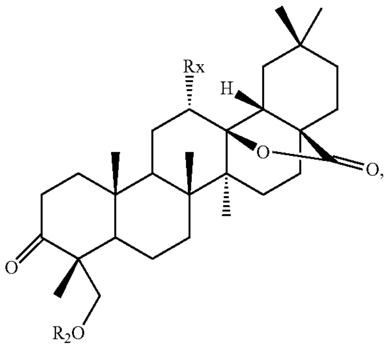

formula (VII)

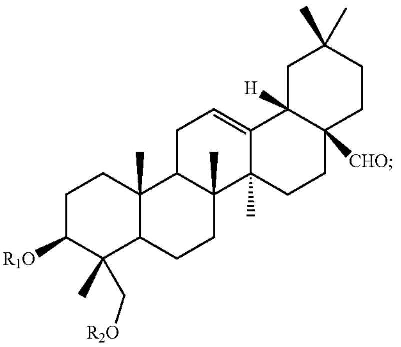

wherein Rx is F, Cl, Br or I.

7. The method of claim 6, wherein the compound of formula (IX) is obtained by converting a compound of formula (X) into the compound of formula (IX) with C—H activation and attaching protecting group sequentially, formula (X)

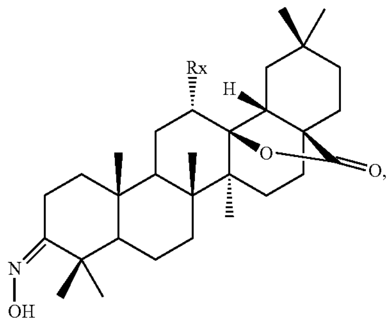

-continued formula (IX)

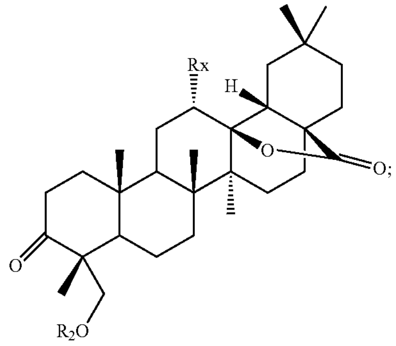

wherein Rx is F, Cl, Br or I.

8. The method of claim 7, wherein the compound of formula (X) is obtained by converting Oleanolic acid into the compound of formula (X) with halolactone oxime formation, formula (X)

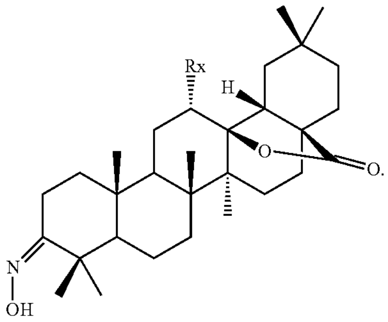

9. The method of claim 3, further comprising a step of converting Hederagenin into the compound of formula (VII) through attaching a protecting group, reduction and oxidation sequentially, formula (VII)

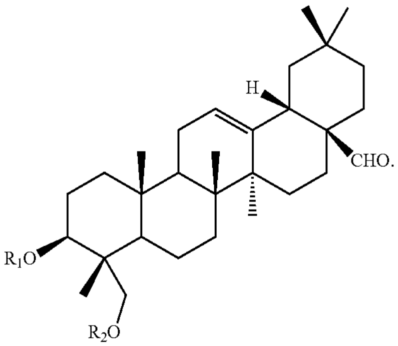

10. The method of claim 3, further comprising a step of oxidizing a compound of formula (XI) into the compound of formula (VII), formula (XI)

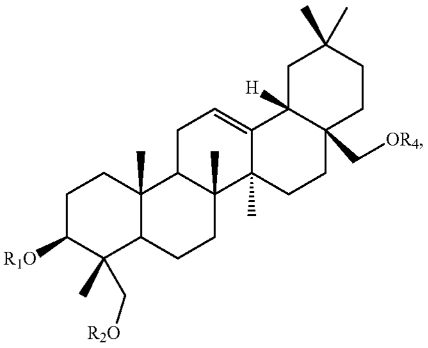

formula (VII)

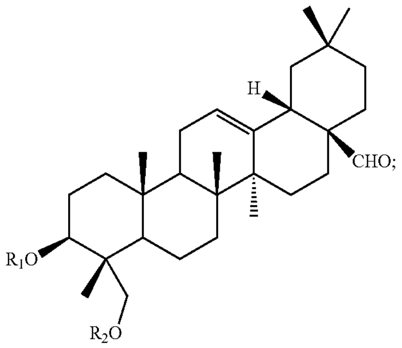

wherein $R_4$ is hydrogen or a protecting group selected from the group consisting of $C_1$-$C_8$ alkyl, $C_2$-$C_8$ alkenyl, $C_2$-$C_8$ alkynyl, ($C_6$-$C_{12}$)aryl($C_1$-$C_8$)alkyl, $C_6$-$C_{12}$ arylacyl, tri($C_1$-$C_8$)alkylsilyl, di($C_1$-$C_8$)alkyl($C_6$-$C_{12}$) arylsilyl, di($C_6$-$C_{12}$)aryl($C_1$-$C_8$)alkylsilyl and tri($C_6$-$C_{12}$)arylsilyl, each of which is substituted with from 0 to 4 substituents independently selected from the group consisting of hydroxy, cyano, halo, halo ($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy.

11. The method of claim 10, further comprising a step of reducing a compound of formula (XII) to the compound of formula (XI), formula (XII)

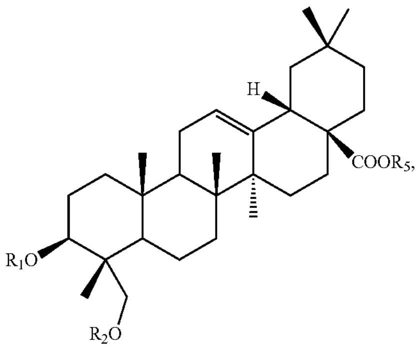

-continued formula (XI)

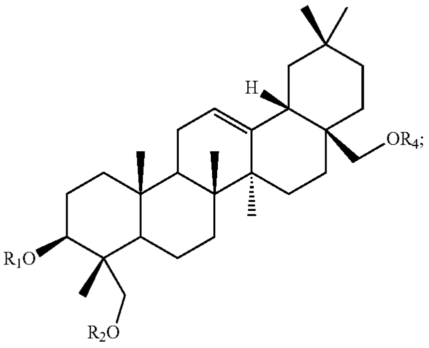

wherein $R_5$ is hydrogen or a group selected from the group consisting of $C_1$-$C_8$ alkyl, $C_2$-$C_8$ alkenyl, $C_2$-$C_8$ alkynyl, ($C_6$-$C_{12}$)aryl($C_1$-$C_8$)alkyl, $C_6$-$C_{12}$ arylacyl, tri($C_1$-$C_8$)alkylsilyl, di($C_1$-$C_8$)alkyl($C_6$-$C_{12}$)arylsilyl, di($C_6$-$C_{12}$)aryl($C_1$-$C_6$) alkylsilyl and tri($C_6$-$C_{12}$)arylsilyl, each of which is substituted with from 0 to 4 substituents independently selected from the group consisting of hydroxy, cyano, halo, halo ($C_1$-$C_6$)alkyl, halo($C_1$-$C_6$)alkyloxy, ($C_1$-$C_6$)alkylthio, $C_1$-$C_6$ alkyl, $C_2$-$C_6$ alkenyl, $C_2$-$C_6$ alkynyl, $C_3$-$C_7$ cycloalkyl and $C_1$-$C_6$ alkoxy.

12. The method of claim 11, wherein comprising a step of converting Hederagenin into the compound of formula (XII) through attaching protecting groups on the hydroxyl groups of Hederagenin, formula (XII)

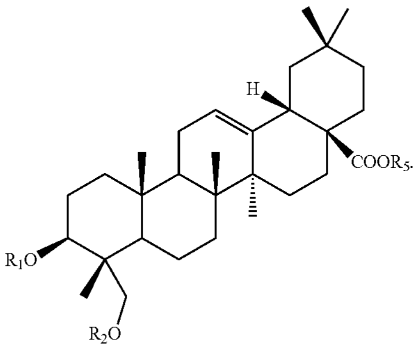

* * * * *